US010893705B2

(12) United States Patent
Hon

(10) Patent No.: US 10,893,705 B2
(45) Date of Patent: Jan. 19, 2021

(54) ELECTRONIC CIGARETTE

(71) Applicant: FONTEM HOLDINGS 1 B.V., Amsterdam (NL)

(72) Inventor: Lik Hon, North Point (HK)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

(21) Appl. No.: 15/904,217

(22) Filed: Feb. 23, 2018

(65) Prior Publication Data

US 2018/0184720 A1 Jul. 5, 2018

Related U.S. Application Data

(60) Continuation of application No. 15/167,690, filed on May 27, 2016, which is a continuation of application
(Continued)

(30) Foreign Application Priority Data

May 16, 2006 (CN) ..................... 2006 2 0090805 U

(51) Int. Cl.
*A24F 47/00* (2006.01)
*F22B 1/28* (2006.01)
(Continued)

(52) U.S. Cl.
CPC .......... *A24F 47/008* (2013.01); *A24F 47/002* (2013.01); *A24F 47/004* (2013.01); *F22B 1/284* (2013.01); *H01M 2/1022* (2013.01); *H01M 2/1055* (2013.01); *H01M 10/0525* (2013.01); *H01M 10/425* (2013.01); *H01M 10/46* (2013.01); *H01M 10/488* (2013.01);
(Continued)

(58) Field of Classification Search
CPC .......... A24D 1/00; A24F 47/008; A24F 47/00
USPC .......................................................... 392/395
See application file for complete search history.

(56) References Cited

U.S. PATENT DOCUMENTS

| 1,147,416 A | 7/1915 | MacDonald |
| 1,775,947 A | 9/1930 | Robinson |
| (Continued) | | |

FOREIGN PATENT DOCUMENTS

| AU | 2005232354 B2 | 10/2005 |
| CN | 2047485 U | 11/1989 |
| (Continued) | | |

OTHER PUBLICATIONS

IP Australia, Application No. AU2007250367, Patent Examination Report No. 1, dated Jul. 30, 2012.
(Continued)

*Primary Examiner* — Ibrahime A Abraham
*Assistant Examiner* — Spencer H. Kirkwood
(74) *Attorney, Agent, or Firm* — Perkins Coie LLP; Kenneth H. Ohriner

(57) ABSTRACT

An electronic cigarette includes a battery assembly and an atomizer assembly within a housing with the battery assembly electrically connected to the atomizer assembly. The housing has one or more air inlets. A liquid storage component is in contact with a porous component of the atomizer assembly, with the porous component having a run-through hole. A heating wire is in an air flow path through the run-through hole.

18 Claims, 8 Drawing Sheets

Related U.S. Application Data

No. 13/740,011, filed on Jan. 11, 2013, now Pat. No. 9,456,632, which is a continuation of application No. 13/079,937, filed on Apr. 5, 2011, now Pat. No. 8,365,742, which is a division of application No. 12/226,818, filed as application No. PCT/CN2007/001575 on May 15, 2007, now Pat. No. 8,156,944.

(51) Int. Cl.

| | | |
|---|---|---|
| *H01M 2/10* | (2006.01) | |
| *H01M 10/0525* | (2010.01) | |
| *H01M 10/42* | (2006.01) | |
| *H01M 10/46* | (2006.01) | |
| *H01M 10/48* | (2006.01) | |
| *H02J 7/00* | (2006.01) | |
| *H05B 1/02* | (2006.01) | |
| *H05B 3/03* | (2006.01) | |
| *H05B 3/06* | (2006.01) | |
| *H05B 3/42* | (2006.01) | |

(52) U.S. Cl.
CPC .............. *H02J 7/00* (2013.01); *H02J 7/0042* (2013.01); *H05B 1/0244* (2013.01); *H05B 1/0291* (2013.01); *H05B 1/0297* (2013.01); *H05B 3/03* (2013.01); *H05B 3/06* (2013.01); *H05B 3/42* (2013.01); *H01M 2220/30* (2013.01)

(56) References Cited

U.S. PATENT DOCUMENTS

| | | | |
|---|---|---|---|
| 1,968,509 A | | 7/1934 | Tiffany |
| 2,057,353 A | | 10/1936 | Whittemore |
| 2,104,266 A | | 1/1938 | McCormick |
| 2,597,195 A | * | 5/1952 | Smith .................... A61L 9/127 392/395 |
| 2,631,219 A | | 3/1953 | Suchy |
| 3,200,819 A | | 8/1965 | Gilbert |
| 3,431,393 A | | 3/1969 | Katsuda |
| 3,479,561 A | | 11/1969 | Janning |
| 3,551,643 A | | 12/1970 | Pricenski et al. |
| 3,685,522 A | | 8/1972 | Kleinhans |
| 3,934,117 A | | 1/1976 | Schladitz |
| 4,171,000 A | | 10/1979 | Uhle |
| 4,207,457 A | | 6/1980 | Haglund et al. |
| 4,228,925 A | | 10/1980 | Mendelovich |
| 4,284,089 A | | 8/1981 | Ray |
| 4,641,053 A | | 2/1987 | Takeda |
| 4,735,217 A | | 4/1988 | Gerth et al. |
| 4,756,318 A | | 7/1988 | Clearman et al. |
| 4,771,295 A | | 9/1988 | Baker |
| 4,771,796 A | | 9/1988 | Myer |
| 4,819,665 A | | 4/1989 | Roberts et al. |
| 4,848,374 A | | 7/1989 | Chard et al. |
| 4,907,606 A | | 3/1990 | Lilja et al. |
| 4,922,901 A | | 5/1990 | Brooks |
| 4,945,929 A | | 8/1990 | Egilmex |
| 4,945,931 A | | 8/1990 | Gori |
| 4,947,874 A | | 8/1990 | Brooks |
| 4,947,875 A | * | 8/1990 | Brooks .................. A24F 47/006 128/202.21 |
| 4,968,263 A | | 11/1990 | Silbernagel |
| 4,981,522 A | | 1/1991 | Nichols |
| 5,042,470 A | | 8/1991 | Kanesaka |
| 5,060,671 A | * | 10/1991 | Counts .................. A24F 47/008 128/202.21 |
| 5,080,114 A | | 1/1992 | Rudolph et al. |
| 5,095,921 A | | 3/1992 | Losee et al. |
| 5,117,482 A | | 5/1992 | Hauber |
| 5,144,962 A | * | 9/1992 | Counts .................. A24F 47/008 128/200.14 |
| 5,159,940 A | | 11/1992 | Hayward et al. |
| 5,190,060 A | | 3/1993 | Gerding et al. |
| 5,224,498 A | | 7/1993 | Deevi et al. |
| 5,249,586 A | | 10/1993 | Morgan et al. |
| 5,261,424 A | | 11/1993 | Sprinkel, Jr. |
| 5,266,746 A | | 11/1993 | Nishihara |
| 5,285,798 A | | 2/1994 | Banerjee et al. |
| 5,322,075 A | | 6/1994 | Deevi et al. |
| 5,388,594 A | | 2/1995 | Counts et al. |
| 5,438,978 A | | 8/1995 | Hardester, III |
| 5,497,791 A | | 3/1996 | Bowen et al. |
| 5,505,214 A | | 4/1996 | Collins et al. |
| 5,512,001 A | | 4/1996 | Kent |
| 5,591,368 A | | 1/1997 | Fleischhauer et al. |
| 5,666,977 A | | 9/1997 | Higgins et al. |
| 5,666,978 A | | 9/1997 | Counts et al. |
| 5,703,633 A | | 12/1997 | Gehrer |
| 5,730,158 A | | 3/1998 | Collins et al. |
| 5,743,251 A | | 4/1998 | Howell et al. |
| 5,746,251 A | | 5/1998 | Bullard |
| 5,799,663 A | | 9/1998 | Gross et al. |
| 5,819,756 A | | 10/1998 | Mielordt |
| 5,865,185 A | * | 2/1999 | Collins .................. A24F 47/008 131/194 |
| 5,878,752 A | | 3/1999 | Adams et al. |
| 5,894,841 A | | 4/1999 | Voges |
| 5,944,025 A | | 8/1999 | Cook |
| 6,010,334 A | | 1/2000 | Mifune et al. |
| 6,040,560 A | | 3/2000 | Fleischhauer et al. |
| 6,041,789 A | | 3/2000 | Bankert et al. |
| 6,095,153 A | | 8/2000 | Kessler et al. |
| 6,125,853 A | | 10/2000 | Susa |
| 6,155,268 A | | 12/2000 | Takeuchi |
| 6,164,287 A | | 12/2000 | White |
| 6,178,969 B1 | | 1/2001 | St. Charles |
| 6,196,218 B1 | | 3/2001 | Voges |
| 6,234,167 B1 | | 5/2001 | Cox |
| 6,354,293 B1 | | 3/2002 | Madison |
| 6,357,671 B1 | | 3/2002 | Cewers |
| 6,443,146 B1 | | 9/2002 | Voges |
| 6,532,965 B1 | | 3/2003 | Abhulimen et al. |
| 6,557,552 B1 | | 5/2003 | Cox |
| 6,598,607 B2 | | 7/2003 | Adiga |
| 6,601,776 B1 | | 8/2003 | Oljaca et al. |
| 6,681,998 B2 | | 1/2004 | Sharpe |
| 6,715,494 B1 | | 4/2004 | McCoy |
| 6,772,756 B2 | | 8/2004 | Shayan |
| 6,803,545 B2 | | 10/2004 | Blake et al. |
| 6,810,883 B2 | | 11/2004 | Felter et al. |
| 6,854,461 B2 | | 2/2005 | Nichols et al. |
| 6,854,470 B1 | | 2/2005 | Pu |
| 7,100,618 B2 | | 9/2006 | Dominguez |
| 7,131,599 B2 | | 11/2006 | Katase |
| 7,726,320 B2 | | 6/2010 | Robinson et al. |
| 7,832,410 B2 | | 11/2010 | Hon |
| 7,845,359 B2 | | 12/2010 | Montaser |
| 7,997,280 B2 | | 8/2011 | Rosenthal |
| 8,156,944 B2 | | 4/2012 | Han |
| 2003/0033055 A1 | | 2/2003 | McRae et al. |
| 2003/0108342 A1 | | 6/2003 | Sherwood et al. |
| 2003/0150451 A1 | * | 8/2003 | Shayan ................ A61M 11/041 128/203.12 |
| 2004/0149282 A1 | | 8/2004 | Hickle |
| 2004/0182403 A1 | | 9/2004 | Andersson et al. |
| 2004/0261802 A1 | | 12/2004 | Griffin et al. |
| 2005/0016550 A1 | | 1/2005 | Katase |
| 2005/0236006 A1 | | 10/2005 | Cowan |
| 2006/0032242 A1 | | 2/2006 | TeGrotenhuis et al. |
| 2006/0175425 A1 | | 8/2006 | McGee et al. |
| 2006/0191546 A1 | | 8/2006 | Takano et al. |
| 2006/0196518 A1 | | 9/2006 | Hon |
| 2008/0276947 A1 | | 11/2008 | Martzel |
| 2009/0095311 A1 | | 4/2009 | Han |
| 2009/0126745 A1 | | 5/2009 | Hon |
| 2009/0151717 A1 | | 6/2009 | Bowen et al. |
| 2009/0188490 A1 | | 7/2009 | Han |
| 2009/0230117 A1 | | 9/2009 | Fernando et al. |
| 2009/0260642 A1 | | 10/2009 | Monsees et al. |
| 2009/0272379 A1 | | 11/2009 | Thorens et al. |
| 2010/0031968 A1 | | 2/2010 | Sheikh et al. |

(56) References Cited

U.S. PATENT DOCUMENTS

| | | | |
|---|---|---|---|
| 2010/0126505 A1 | 5/2010 | Rinker | |
| 2010/0181387 A1 | 7/2010 | Zaffaroni et al. | |
| 2010/0200008 A1 | 8/2010 | Taieb | |
| 2010/0242974 A1 | 9/2010 | Pan | |
| 2010/0307518 A1 | 12/2010 | Wang | |
| 2011/0005535 A1 | 1/2011 | Xiu | |
| 2011/0011396 A1 | 1/2011 | Fang | |
| 2011/0036346 A1 | 2/2011 | Cohen et al. | |
| 2012/0111347 A1 | 5/2012 | Hon | |

FOREIGN PATENT DOCUMENTS

| | | | | |
|---|---|---|---|---|
| CN | 2084236 | U | 9/1991 | |
| CN | 1135860 | A | 11/1996 | |
| CN | 1196660 | A | 11/1996 | |
| CN | 2293957 | Y | 10/1998 | |
| CN | 1233436 | A | 11/1999 | |
| CN | 1252961 | A | 5/2000 | |
| CN | 1575673 | A | 2/2005 | |
| CN | 2719043 | Y | 8/2005 | |
| CN | 2777995 | Y | 5/2006 | |
| CN | 1284493 | C | 11/2006 | |
| CN | 2870485 | Y | 2/2007 | |
| CN | 200997909 | Y | 1/2008 | |
| CN | 101116542 | A | 2/2008 | |
| CN | 101176805 | A | 5/2008 | |
| CN | 201067079 | Y | 6/2008 | |
| CN | 201079011 | Y | 7/2008 | |
| CN | 201085044 | Y | 7/2008 | |
| CN | 201379072 | Y | 1/2010 | |
| CN | 201797997 | U | 4/2011 | |
| CN | 2887086 | U | 11/2011 | |
| CN | 202026802 | U | 11/2011 | |
| CN | 202026804 | U | 11/2011 | |
| DE | 10051792 | A1 | 5/2002 | |
| DE | 102006004484 | A1 | 8/2007 | |
| EP | 57243 | A1 | 8/1982 | |
| EP | 192950 | A1 | 3/1986 | |
| EP | 230420 | A1 | 8/1987 | |
| EP | 0125210 | B1 | 12/1987 | |
| EP | 295122 | A2 | 12/1988 | |
| EP | 342538 | A2 | 11/1989 | |
| EP | 358002 | A2 | 3/1990 | |
| EP | 295122 | B1 | 1/1992 | |
| EP | 545186 | A2 | 6/1993 | |
| EP | 703735 | A1 | 4/1996 | |
| EP | 824927 | A2 | 2/1998 | |
| EP | 845220 | A1 | 6/1998 | |
| EP | 893071 | A1 | 1/1999 | |
| EP | 951219 | A1 | 10/1999 | |
| EP | 951219 | B1 | 11/2002 | |
| EP | 2018886 | A1 | 1/2009 | |
| GB | 588117 | A | 5/1947 | |
| GB | 1528391 | A | 10/1978 | |
| JP | 64000498 | U | 1/1989 | |
| JP | H0593516 | A | 4/1993 | |
| JP | 6114105 | A | 4/1994 | |
| JP | 7506999 | | 8/1995 | |
| JP | 9075058 | A | 3/1997 | |
| UA | 47514 | C2 | 12/1997 | |
| WO | 1994009842 | A1 | 5/1994 | |
| WO | 1994021317 | A1 | 9/1994 | |
| WO | 1997040876 | A2 | 11/1997 | |
| WO | 1997048293 | A1 | 12/1997 | |
| WO | 1998017130 | A1 | 4/1998 | |
| WO | WO 9817130 | A1 * | 4/1998 | ........... A24F 47/008 |
| WO | 2000049901 | A2 | 8/2000 | |
| WO | 2001005459 | A1 | 1/2001 | |
| WO | 2002061701 | A1 | 8/2002 | |
| WO | 2003022364 | A1 | 3/2003 | |
| WO | 2003034847 | A1 | 5/2003 | |
| WO | 2003055486 | A1 | 7/2003 | |
| WO | 2003101454 | A1 | 12/2003 | |
| WO | 2004001407 | A1 | 12/2003 | |
| WO | 2004023222 | A2 | 3/2004 | |
| WO | 2004080216 | A1 | 9/2004 | |
| WO | 2004095955 | A1 | 11/2004 | |
| WO | 2005099494 | A1 | 10/2005 | |
| WO | 2006082571 | A1 | 8/2006 | |
| WO | 2006124757 | A2 | 11/2006 | |
| WO | 2007078273 | A1 | 7/2007 | |
| WO | 2008077271 | A1 | 7/2008 | |
| WO | 2008130813 | A1 | 10/2008 | |
| WO | 2009118085 | A1 | 10/2009 | |
| WO | 2009135729 | A1 | 11/2009 | |
| WO | 2010052323 | A2 | 5/2010 | |
| WO | 2010145468 | A1 | 12/2010 | |
| WO | 2010145805 | A1 | 12/2010 | |
| WO | 2011010334 | A1 | 1/2011 | |
| WO | 2011022431 | A1 | 2/2011 | |

OTHER PUBLICATIONS

EPO, Opposition of EP2878215 (Application No. 14173781.7), Exam Report, dated Nov. 23, 2017.
EPO, Opposition of EP2878215 (Application No. 14173781.7), Provisional Decision in advance of Oral Hearing, Aug. 13, 2018.
EPO, Opposition of EP2878215 (Application No. 14173781.7), Proprietor's Response, Jul. 4, 2017.
EPO, Opposition of EP2878215 (Application No. 14173781.7), A3—First Affidavit of Min Xu dated Sep. 7, 2015, filed with Proprietor's Response, Jul. 4, 2017.
EPO, Opposition of EP2878215 (Application No. 14173781.7), A4—Second Affidavit of Min Xu dated Dec. 17, 2015, filed with Proprietor's Response, Jul. 4, 2017.
EPO, Opposition of EP2878215 (Application No. 14173781.7), A5—Third Affidavit of Min Xu dated Jun. 13, 2016, filed with Proprietor's Response, Jul. 4, 2017.
EPO, Opposition of EP2878215 (Application No. 14173781.7), A6—Affidavit of Aimei Xu dated Jul. 27, 2016, filed with Proprietor's Response, Jul. 4, 2017.
USPTO, U.S. Appl. No. 12/226,818, Notice of Allowance, dated Dec. 6, 2011.
USPTO, U.S. Appl. No. 13/079,937, Notice of Allowance, dated Nov. 14, 2012.
USPTO, U.S. Appl. No. 13/740,011, Notice of Allowance, dated Jun. 21, 2016.
USPTO, U.S. Appl. No. 13/740,011, Corrected Notice of Allowance, dated Jun. 29, 2016.
USPTO, U.S. Appl. No. 14/244,376, Notice of Allowance, dated Mar. 15, 2016.
USPTO, U.S. Appl. No. 15/167,659, Notice of Allowance, dated Apr. 21, 2017.
USPTO, U.S. Appl. No. 15/167,659, Corrected Notice of Allowability, dated Jun. 13, 2017.
USPTO, U.S. Appl. No. 15/167,659, Corrected Notice of Allowability, dated Jul. 13, 2017.
USPTO, U.S. Appl. No. 15/167,659, Corrected Notice of Allowability, dated Oct. 4, 2017.
USPTO, U.S. Appl. No. 95/002,235, Non-Final Office Action in Inter Partes Reexamination, CN03111582.9, English Machine Translation corresponding to priority document of Hon '955, dated Nov. 27, 2012.
USPTO, U.S. Appl. No. 95/002,235, Non-Final Office Action in Inter Partes Reexamination, CN200420031182, English Machine Translation corresponding to priority document of Hon '494, dated Nov. 27, 2012.
USPTO, U.S. Appl. No. 95/002,235, Right of Appeal Notice in Inter Partes Reexamination, Oct. 16, 2018.
USPTO PTAB, IPR2016-01692, Paper 8, Decision Instituting inter partes review, Mar. 7, 2017.
Joyetech Deutschland GMBH, Opposition to EP2878215, Jan. 27, 2017.
Joyetech Deutschland GMBH, Opposition to EP2878215, D1—U.S. Pat. No. 2,057,353 A, Jan. 27, 2017.
Joyetech Deutschland GMBH, Opposition to EP2878215, D2—EP0845220A, Jan. 27, 2017.

(56) References Cited

OTHER PUBLICATIONS

Joyetech Deutschland GMBH, Opposition to EP2878215, D3—CN2719043YA1, Jan. 27, 2017.
Joyetech Deutschland GMBH, Opposition to EP2878215, D3a—EP1736065A1, Jan. 27, 2017.
Joyetech Deutschland GMBH, Opposition to EP2878215, D3b—CN2719043Y—English Translation, Jan. 27, 2017.
Joyetech Deutschland GMBH, Opposition to EP2878215, D4—U.S. Pat. No. 3,934,117 A, Jan. 27, 2017.
Joyetech Deutschland GMBH, Opposition to EP2878215, D5—U.S. Pat. No. 5,117,482 A, Jan. 27, 2017.
Joyetech Deutschland GMBH, Opposition to EP2878215, D6—U.S. Pat. No. 6,681,998 B2, Jan. 27, 2017.
Joyetech Deutschland GMBH, Opposition to EP2878215, D7—U.S. Pat. No. 6,557,552 B1, Jan. 27, 2017.
Joyetech Deutschland GMBH, Opposition to EP2878215, D8—EP0703735B1, Jan. 27, 2017.
Joyetech Deutschland GMBH, Opposition to EP2878215, D9—EP0893071A1, Jan. 27, 2017.
Joyetech Deutschland GMBH, Opposition to EP2878215, D10—Wikepedia "Heating Element", Jan. 27, 2017.
Joyetech Deutschland GMBH, Opposition to EP2878215, D11—EP1618803A1, Jan. 27, 2017.
Joyetech Deutschland GMBH, Opposition to EP2878215, D12—EP0358114A2, Jan. 27, 2017.
Joyetech Deutschland GMBH, Opposition to EP2878215, D13—EP2018886A1, Jan. 27, 2017.
Joyetech Deutschland GMBH, Opposition to EP2878215, EP1—EP2878215B1, Jan. 27, 2017.
Joyetech Deutschland GMBH, Opposition to EP2878215, EP2—WO20070131449A1, Jan. 27, 2017.
Joyetech Deutschland GMBH, Opposition to EP2878215, EP2a—EP2022349A1 (Parent application), Jan. 27, 2017.
Joyetech Deutschland GMBH, Opposition to EP2878215, EP2b—WO20070131449A1 English Translation, Jan. 27, 2017.
Joyetech Deutschland GMBH, Opposition to EP2878215, EP2c—EP2878215A1 (published Engl. Language div appl.), Jan. 27, 2017.
Joyetech Deutschland GMBH, Opposition to EP2878215, EP2d Comparison of the Specifications of EP2878215A1 and EP2022349A1, Jan. 27, 2017.
Joyetech Deutschland GMBH, Opposition to EP2878215, EP3—priority application CN2006290805, Jan. 27, 2017.
Joyetech Deutschland GMBH, Opposition to EP2878215, EP3a—CN2006-20090805 (English Translation), Jan. 27, 2017.
Joyetech Deutschland GMBH, Opposition to EP2878215, EP4—Decision Revoking EP 2022349B1, Jan. 27, 2017.
Philip Morris Products S.A., Opposition to EP2878215, Jan. 27, 2017.
Philip Morris Products S.A., Opposition to EP2878215, A1—EPO Affidavit-Guo Huixin, Jan. 27, 2017.
Philip Morris Products S.A., Opposition to EP2878215, A2—UK Expert Report of Guo, Jan. 27, 2017.
Philip Morris Products S.A., Opposition to EP2878215, D1—EP2022350A1, Jan. 27, 2017.
Philip Morris Products S.A., Opposition to EP2878215, D2—EP2018886A1, Jan. 27, 2017.
Philip Morris Products S.A., Opposition to EP2878215, D3—U.S. Pat. No. 2,057,353 A1, Jan. 27, 2017.
Philip Morris Products S.A., Opposition to EP2878215, D4—EP0893071A1, Jan. 27, 2017.
Philip Morris Products S.A., Opposition to EP2878215, D5—WO2005099494A1, Jan. 27, 2017.
Philip Morris Products S.A., Opposition to EP2878215, D5a—EP1736065A1, Jan. 27, 2017.
Philip Morris Products S.A., Opposition to EP2878215, D6—CN2777995Y, Jan. 27, 2017.
Philip Morris Products S.A., Opposition to EP2878215, D6a—CN2777995Y English Translation, Jan. 27, 2017.
Philip Morris Products S.A., Opposition to EP2878215, D7—U.S. Pat. No. 4,947,874 A, Jan. 27, 2017.
Philip Morris Products S.A., Opposition to EP2878215, D8—U.S. Pat. No. 5,894,841 A, Jan. 27, 2017.
Philip Morris Products S.A., Opposition to EP2878215, D9—EP0845220A, Jan. 27, 2017.
Philip Morris Products S.A., Opposition to EP2878215, D10—U.S. Pat. No. 3,934,117 A, Jan. 27, 2017.
Philip Morris Product S.A., Opposition to EP2878215, D11—U.S. Pat. No. 1,968,509 A, Jan. 27, 2017.
Philip Morris Products S.A., Opposition to EP2878215, D12—GB588117A, Jan. 27, 2017.
Philip Morris Products S.A., Opposition to EP2878215, Dec. 1—Written Decision (EPO), Jan. 27, 2017.
Philip Morris Products S.A., Opposition to EP2878215, Dec. 2—UK Decision, Jan. 27, 2017.
Philip Morris Products S.A., Opposition to EP2878215, EP1—Opposed Patent EP2878215B1, Jan. 27, 2017.
Philip Morris Products S.A., Opposition to EP2878215, EP2—WO20070131449A1, Jan. 27, 2017.
Philip Morris Products S.A., Opposition to EP2878215, EP2a—EP2022349A1 (Parent application), Jan. 27, 2017.
Philip Morris Products S.A., Opposition to EP2878215, EP2b—WO20070131449A1 English Translation, Jan. 27, 2017.
Philip Morris Products S.A., Opposition to EP2878215, EP2c—EP2878215A1 (published Engl. Language div appl.), Jan. 27, 2017.
Philip Morris Products S.A., Opposition to EP2878215, EP2d—EP2022349B1 (Revoked parent patent), Jan. 27, 2017.
Philip Morris Products S.A., Opposition to EP2878215, EP3—CN2006-20090805Y (CN201067079Y), Jan. 27, 2017.
Philip Morris Products S.A., Opposition to EP2878215, EP3a—CN201067079Y English Translation, Jan. 27, 2017.
Mexican Institute of Intellectual Property, Application No. Mx/a/2017/009524, Exam Report, dated May 23, 2018.
R.J. Reynolds Vapor Company, Final Invalidity Contentions served in *Fontem Holdings B.V.* v. *R.J. Reynolds Vapor Company*, U.S. District Court for the Middle District of North Carolina, Case No. 16-cv-1255 and consolidated cases (relating to U.S. Pat. Nos. 8,365,742, 8,490,628, 8,893,726, 8,899,239, 8,326,548, 8,326,549, and 9,370,205), May 7, 2018.
R.J. Reynolds Vapor Company, Final Invalidity Elections served in *Fontem Holdings B.V.* v. *R.J. Reynolds Vapor Company*, U.S. District Court for the Middle District of North Carolina, Case No. 16-cv-1255 and consolidated cases (relating to U.S. Pat. Nos. 8,365,742, 8,490,628, 8,893,726, 8,899,239, 8,326,548, 8,326,549, and 9,370,205), May 7, 2018.
R.J. Reynolds Vapor Company, Final Invalidity Contentions, 16-cv-1255 and consolidated cases, Amended Exhibit A (U.S. Pat. No. 8,365,742), May 7, 2018.
R.J. Reynolds Vapor Company, Final Invalidity Contentions, 16-cv-1255 and consolidated cases, Amended Exhibit E (U.S. Pat. No. 9,326,548), May 7, 2018.
R.J. Reynolds Vapor Company, Final Invalidity Contentions served in *Fontem Holdings B.V.* v. *R.J. Reynolds Vapor Company*, U.S. District Court for the Middle District of North Carolina, Case No. 16-cv-1255 and consolidated cases (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Elections served in *Fontem Holdings B.V.* v. *R.J. Reynolds Vapor Company*, U.S. District Court for the Middle District of North Carolina, Case No. 16-cv-1255 and consolidated cases (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Contentions, 16-cv-1255 and consolidated cases, Amended Exhibit H (U.S. Pat. No. 9,456,632), May 7, 2018.
USPTO, U.S. Appl. No. 15/167,690, Non-Final Office Action, dated Dec. 29, 2016.
USPTO, U.S. Appl. No. 15/167,690, Final Office Action, dated Apr. 26, 2017.
USPTO, U.S. Appl. No. 15/167,690, Non-Final Office Action, dated Jul. 26, 2018.
USPTO, U.S. Appl. No. 15/996,969, Non-Final Office Action, dated Aug. 15, 2018.

(56) References Cited

OTHER PUBLICATIONS

USPTO, U.S. Appl. No. 95/002,235, Office Action in Inter Partes Reexamination, dated Mar. 14, 2018.
Anonymous, Third Party Observation for EP Application No. 10740882, Oct. 3, 2013.
Anonymous, Third Party Observations for EP Application No. 10740882, Apr. 11, 2014.
CB Distributors Inc. and DR Distributors, LLC, IPR2013-00387, Paper 1, Petition for Inter Partes Review of U.S. Pat. No. 8,156,944, Jun. 27, 2013.
CB Distributors Inc. and DR Distributors, LLC, IPR2013-00387, Ex. 1001—U.S. Pat. No. 8,156,944 to Han, Jun. 27, 2013.
CB Distributors Inc. and DR Distributors, LLC, IPR2013-00387, Ex. 1002—Request for Certificate of Correction dated Jun. 11, 2012, Jun. 27, 2013.
CB Distributors Inc. and DR Distributors, LLC, IPR2013-00387, Ex. 1003—WO 2007/131449 A1 to Hon, Jun. 27, 2013.
CB Distributors Inc. and DR Distributors, LLC, IPR2013-00387, Ex. 1004—CN U.S. Pat. No. 2,719,043, Jun. 27, 2013.
CB Distributors Inc. and DR Distributors, LLC, IPR2013-00387, Ex. 1005—CN Patent Application No. 200620090805, Jun. 27, 2013.
CB Distributors Inc. and DR Distributors, LLC, IPR2013-00387, Ex. 1006—Certified English Translation of CN Patent Application No. 200620090805 dated Oct. 6, 2011, Jun. 27, 2013.
CB Distributors Inc. and DR Distributors, LLC, IPR2013-00387, Ex. 1007—WO 2004/095955 A1 to Hon, Jun. 27, 2013.
CB Distributors Inc. and DR Distributors, LLC, IPR2013-00387, Ex. 1008—WO 2005/099494 A1 to Hon, Jun. 27, 2013.
CB Distributors Inc. and DR Distributors, LLC, IPR2013-00387, Ex. 1009—Certified English Translation of WO 2005/099494 A1 to Hon dated Jun. 17, 2013, Jun. 27, 2013.
CB Distributors Inc. and DR Distributors, LLC, IPR2013-00387, Ex. 1010—Office Action dated Feb. 2, 2011, Jun. 27, 2013.
CB Distributors Inc. and DR Distributors, LLC, IPR2013-00387, Ex. 1011—Response to Office Action dated Feb. 22, 2011, Jun. 27, 2013.
CB Distributors Inc. and DR Distributors, LLC, IPR2013-00387, Ex. 1012—Office Action dated Apr. 12, 2011, Jun. 27, 2013.
CB Distributors Inc. and DR Distributors, LLC, IPR2013-00387, Ex. 1013—Response to Office Action dated Oct. 12, 2011, Jun. 27, 2013.
CB Distributors Inc. and DR Distributors, LLC, IPR2013-00387, Ex. 1014—Inter Partes Reexamination Request dated Sep. 13, 2012, Jun. 27, 2013.
CB Distributors Inc. and DR Distributors, LLC, IPR2013-00387, Ex. 1015—Order Granting Reexamination dated Nov. 27, 2012, Jun. 27, 2013.
CB Distributors Inc. and DR Distributors, LLC, IPR2013-00387, Ex. 1016—Office Action dated Nov. 27, 2012, Jun. 27, 2013.
CB Distributors Inc. and DR Distributors, LLC, IPR2013-00387, Ex. 1017—Response to Office Action dated Jan. 28, 2013, Jun. 27, 2013.
CB Distributors Inc. and DR Distributors, LLC, IPR2013-00387, Ex. 1018—Third Party Response dated Feb. 27, 2013, Jun. 27, 2013.
CB Distributors Inc. and DR Distributors, LLC, IPR2013-00387, Ex. 1019—WO 2007/078273 A1 to Liu, Jun. 27, 2013.
CB Distributors Inc. and DR Distributors, LLC, IPR2013-00387, Ex. 1020—EP 0845220 A1 to Susa et al., Jun. 27, 2013.
Chen, Zhiyong, English Translation of Request for Invalidation of CN200620090805.0, Jun. 6, 2013.
*CN Creative and Intellicig USA, Ruyan v. Smoking Everywhere et al.* CV11-6268 Invalidity Contentions, Apr. 12, 2012.
CN03111582.9, English Machine Translation corresponding to priority document of Hon '955.
CN200420031182, English Machine Translation corresponding to priority document of Hon '494.
Collins, John M., Expert Report—Invalidity (Excerpts), CV14-01645, Jun. 18, 2015.
Collins, John M., Expert Report—Invalidity, CV14-01645—Appendix E—'742, Jun. 18, 2015.
Cyphert Gil DBA NU1S, *Ruyan v. Smoking Everywhere et al.* CV11-0367 Invalidity Contentions, Apr. 11, 2012.
Eisenfuhr Speiser Partgmbb, Notice and Grounds of Opposition to European Patent No. EP2022349, Apr. 30, 2015.
Eisenfuhr Spieser Part GMBH, Opposition to EP2022349—Additional Observations, Aug. 5, 2016.
Eisenfuhr Spieser Part GMBH, Opposition to EP2022349—Annex 1 to Additional Observations, Affidavit of Aimei Xu, Aug. 5, 2016.
European Patent Office, Decision Revoking European Patent No. EP2022349, Oct. 17, 2016, 23 pgs.
European Patent Office, Examination Report for EP 14155503.7, dated Oct. 25, 2017, 5 pgs.
European Patent Office, extended European Search Report for EP07721148, dated Dec. 6, 2010.
European Patent Office, extended European Search Report for EP11001479, dated Jul. 4, 2011.
European Patent Office, extended European Search Report for EP14155503.7, dated Feb. 3, 2015.
European Patent Office, Extended European Search Report for EP14173781.7, dated Apr. 22, 2015, 6 pgs.
European Patent Office, Extended European Search Report for EP16158159.0, dated Jul. 12, 2016, 5 pgs.
European Patent Office, Observations by Third Parties in EP Patent Application No. 14173781.7, Jan. 13, 2016.
European Patent Office, partial European Search Report for EP14155503.7, dated Sep. 1, 2014.
European Patent Office, Supplemental Extended European Search Report for EP04718242, dated Jul. 27, 2007.
European Patent Office, Supplemental Partial Extended European Search Report for EP04718242, dated May 22, 2007.
European Patent Office, Supplementary European Search Report and Search Opinion for EP 10740882.5, dated Oct. 16, 2013.
European Patent Office, Supplementary Extended European Search Report for EP05729107, dated Jul. 31, 2007.
European Patent Office, Supplementary Partial Extended European Search Report for EP05729107, dated May 22, 2007.
FIN Branding Group, LLC, Request for Inter Partes Reexamination of U.S. Pat. No. 8,156,944, Sep. 13, 2012.
FIN Branding Group, LLC, Third Party Response to Amendment including Submission of Prior Arts and Misc. Statement Per 37 CFR 1.948 and Oljaca 6601776 in Reexamination of U.S. Pat. No. 8,156,944, Feb. 27, 2013.
High Court of Justice, Great Britain, *Nicocigs Limited v. Fontem Holdings 1 B.V. et al.*, Claim No. HP-2015-000027, Approved Judgment Revoking EP (UK) 2022349, Sep. 2, 2016.
India Patent Office, First Examination Report for IN 8528/DELNP/2008, dated Mar. 27, 2014.
Insmoke AG, Notice and Grounds of Opposition to European Patent No. EP202234942122, Apr. 28, 2015.
Intellectual Property India, First Examination Report for counterpart Indian Application No. 8528/DELNP/2008, dated Mar. 27, 2014.
Intellectual Property Office of New Zealand, Exam Report for NZ572309, dated Apr. 21, 2010.
Introduction to selecting and using electronic components, ISBN7-111-13752-3.
IP Australia, Exam Report for AU2004234199, dated Aug. 14, 2000.
IP Australia, Examination Report for SG 200505930-8, dated May 4, 2006.
IP Australia, Examination Report for SG200604498-6, dated Apr. 16, 2008.
IP Australia, Patent Examination Report for Patent Application No. 2014208287, dated Aug. 5, 2016, 4 pgs.
IP Australia, Patent Examination Report No. 1 for AU 2010213240, dated Aug. 5, 2013.
IP Australia, Patent Examination Report No. 1 for AU2007250367, dated Jul. 30, 2012.
IP Australia, Patent Examination Report No. 1 for AU2007250368, dated Aug. 9, 2012.
Israel Patent Office, Exam Report for IL194768, dated Nov. 12, 2014.

(56) References Cited

OTHER PUBLICATIONS

ITC Limited, Opposition to Grant of Indian Patent Application No. 8528/DELNP/2008, served on Applicant's Indian Counsel Oct. 18, 2016 (filed Sep. 10, 2014).
ITC Limited, Opposition to Grant of Indian Patent Application No. 8528/DELNP/2008, Annexure A—Complete specification application No. 8528/DELNP/2008, Sep. 10, 2014.
ITC Limited, Opposition to Grant of Indian Patent Application No. 8528/DELNP/2008, Annexure A1—INPADOC family list for WO2007131449, Sep. 10, 2014.
ITC Limited, Opposition to Grant of Indian Patent Application No. 8528/DELNP/2008, Annexure A2—International Search Report and Preliminary Examination Report for PCT/CN2007/001575 (WO counterpart of impugned application), Sep. 10, 2014.
ITC Limited, Opposition to Grant of Indian Patent Application No. 8528/DELNP/2008, Exhibit 1—EP1736065 (English equivalent of CN2719043), Sep. 10, 2014.
ITC Limited, Opposition to Grant of Indian Patent Application No. 8528/DELNP/2008, Exhibit 2—U.S. Pat. No. 5,799,663, Sep. 10, 2014.
ITC Limited, Opposition to Grant of Indian Patent Application No. 8528/DELNP/2008, Exhibit 3—EP0845220, Sep. 10, 2014.
ITC Limited, Opposition to Grant of Indian Patent Application No. 8528/DELNP/2008, Exhibit 4—EP0951219, Sep. 10, 2014.
Japanese Patent Office, Office Action for JP2006504199, dated Oct. 30, 2009.
Joyetech Deutschland GMBH, Notice and Grounds of Opposition against European Patent No. EP2022349, Mar. 10, 2015.
Joyetech Deutschland GMBH, Opposition to EP2022349—Additional Observations, Aug. 8, 2016.
JT International S.A., Petition for Inter Partes Review of U.S. Pat. No. 8,365,742—IPR2015-01587, Paper 1, Jul. 14, 2015.
JT International S.A., IPR2015-01587, Ex. 1001, U.S. Pat. No. 8,365,742 ("'742 patent"), Jul. 14, 2015.
JT International S.A., IPR2015-01587, Ex. 1002, Declaration of Jeffrey A. Schuster, Ph.D., Jul. 14, 2015.
JT International S.A., IPR2015-01587, Ex. 1003, U.S. Pat. No. 6,155,268 ("Takeuchi"), Jul. 14, 2015.
JT International S.A., IPR2015-01587, Ex. 1004, U.S. Pat. No. 6,234,167 ("Cox"), Jul. 14, 2015.
JT International S.A., IPR2015-01587, Ex. 1005, U.S. Pat. No. 4,947,874 ("Brooks"), Jul. 14, 2015.
JT International S.A., IPR2015-01587, Ex. 1006, U.S. Pat. No. 2,057,353 ("Whittemore"), Jul. 14, 2015.
JT International S.A., IPR2015-01587, Ex. 1007, EP 0 845 220 ("Susa"), Jul. 14, 2015.
JT International S.A., IPR2015-01587, Ex. 1008, WO 2007/078273 A1 ("Liu"), Jul. 14, 2015.
JT International S.A., IPR2015-01587, Ex. 1009, '742 Prosecution History, Preliminary Amendment, dated Jul. 14, 2015.
JT International S.A., IPR2015-01587, Ex. 1010, '742 Prosecution History, Non-final Office Action, dated Jul. 14, 2015.
JT International S.A., IPR2015-01587, Ex. 1011, '742 Prosecution History, Amendment, dated Jul. 14, 2015.
JT International S.A., IPR2015-01587, Ex. 1012, '742 Prosecution History, Supplemental Amendment, dated Jul. 14, 2015.
JT International S.A., IPR2015-01587, Ex. 1013, '742 Prosecution History, Examiner Interview Summary, dated Jul. 14, 2015.
JT International S.A., IPR2015-01587, Ex. 1014, '742 Prosecution History, Notice of Allowance, dated Jul. 14, 2015.
JT International S.A., IPR2015-01587, Ex. 1015, '742 Prosecution History, Certificate of Correction, Jul. 14, 2015.
JT International S.A., IPR2015-01587, Ex. 1016, Fontem Litigation Joint Claim Construction Chart, Jul. 14, 2015.
JT International S.A., IPR2015-01587, Ex. 1017, Claim Construction Rulings in CV 14-1645 , Jul. 14, 2015.
JT International S.A., IPR2015-01587, Ex. 1018, Webster's New World Collegiate Dictionary ("detach"), Jul. 14, 2015.
JT International S.A., IPR2015-01587, Ex. 1019, Oxford American Dictionary & Thesaurus ("frame") , Jul. 14, 2015.
JT International S.A., IPR2015-01587, Ex. 1020, McGraw-Hill Dictionary of Scientific and Technical Terms (5th ed. 1994) ("assembly") ("component") ("porous") , Jul. 14, 2015.
JT International S.A., IPR2015-01587, Ex. 1021, Academic Press Dictionary ("permeability") ("solid"), Jul. 14, 2015.
JT International S.A., IPR2015-01587, Ex. 1022, American Heritage Dictionary ("atomize") ("end") ("substantial"), Jul. 14, 2015.
JT International S.A., IPR2015-01587, Ex. 1023, Merriam-Webster. com ("aerosol") ("atomizer") ("permeable") ("porous"), Jul. 14, 2015.
JT International S.A., Notice and Grounds of Opposition against European Patent No. EP20223494, Apr. 30, 2015.
Khan, Sirajuddin, Son of Samsuddin Khan, Pre-grant opposition ("representation") against counterpart Indian Application No. 8528/DELNP/2008, Jun. 20, 2014.
Korean Intellectual Property Office, Notice of Preliminary Rejection for KR1020057009767, dated Jul. 27, 2009.
Korean Intellectual Property Office, Office Action for KR1020087026879, dated Jun. 9, 2011.
Macau Patent Office, Official Communication for MOI121, dated Apr. 17, 2009.
Malaysian Patent Office, Examination Report for MY PI 20041407, dated Sep. 28, 2007.
Manual for Electric Engineers, 2nd Ed, Mar. 2000.
Manual for Mechanical Designers, 4th Ed, Jan. 2002.
Materials Manual-Nonmetal, Jul. 1, 1985.
Mexican Institute of Industrial Property, Exam Report for MX/a/2008/013526, dated Jul. 15, 2011.
Nicoventures Holdings Limited, Notice and Grounds of Opposition to European Patent No. EP2022349, Apr. 30, 2015.
Njoy, Inc. et al., Attachment A to Defendant's Joint Invalidity Contentions—Claim Charts for U.S. Pat. No. 8,365,742, Aug. 7, 2014.
Njoy, Inc. et al., Defendants' Joint Invalidity Contentions, Case No. CV-14-01645 etc., Aug. 7, 2014.
Nu Mark LLC, Petition for Inter Partes Review of U.S. Pat. No. 8,365,742—IPR2016-01303, Paper 1, Jun. 28, 2016.
Nu Mark LLC, IPR2016-01303, Ex.1001 U.S. Pat. No. 8,365,742 ("the 742 Patent"), Jun. 28, 2016.
Nu Mark LLC, IPR2016-01303, Ex.1002 Excerpts of the prosecution history for U.S. Pat. No. 8,365,742, Jun. 28, 2016.
Nu Mark LLC, IPR2016-01303, Ex.1003 Declaration of John M. Collins, Ph.D. ("Collins Decl."), Jun. 28, 2016.
Nu Mark LLC, IPR2016-01303, Ex.1004 U.S. Pat. No. 6,155,268 ("Takeuchi"), Jun. 28, 2016.
Nu Mark LLC, IPR2016-01303, Ex.1005 U.S. Pat. No. 2,057,353 ("Whittemore"), Jun. 28, 2016.
Nu Mark LLC, IPR2016-01303, Ex.1006 U.S. Pat. No. 4,947,874 ("Brooks"), Jun. 28, 2016.
Nu Mark LLC, IPR2016-01303, Ex.1007 Docket entry #65 from *Fontem Ventures, B.V., et al. v. Njoy, Inc., et al.*, 2:14-cv-01645 (C.D. Cal.) ("Rulings on Claim Construction"), Jun. 28, 2016.
Nu Mark LLC, IPR2016-01303, Ex.1008 U.S. Patent Application No. 2006/0093977 A1 ("Pellizzari I"), Jun. 28, 2016.
Nu Mark LLC, IPR2016-01303, Ex.1009 U.S. Pat. No. 7,059,307 ("Pellizzari II"), Jun. 28, 2016.
Nu Mark LLC, IPR2016-01303, Ex.1010 U.S. Pat. No. 5,894,841 ("Voges"), Jun. 28, 2016.
Nu Mark LLC, IPR2016-01303, Ex.1011 U.S. Pat. No. 5,743,251 ("Howell"), Jun. 28, 2016.
Nu Mark LLC, IPR2016-01303, Ex.1012 U.S. Pat. No. 2,461,664 ("Smith"), Jun. 28, 2016.
Nu Mark LLC, IPR2016-01303, Ex.1013 U.S. Pat. No. 3,234,357 ("Eberhard"), Jun. 28, 2016.
Nu Mark LLC, IPR2016-01303, Ex.1014 U.S. Pat. No. 5,745,985 ("Ghosh"), Jun. 28, 2016.
Nu Mark LLC, IPR2016-01303, Ex.1015 U.S. Pat. No. 4,676,237 ("Wood"), Jun. 28, 2016.
Nu Mark LLC, IPR2016-01303, Ex.1016 U.S. Pat. No. 4,945,448 ("Bremenour"), Jun. 28, 2016.
Nu Mark LLC, IPR2016-01303, Ex.1017 U.S. Pat. No. 2,442,004 ("Hayward-Butt"), Jun. 28, 2016.

(56) References Cited

OTHER PUBLICATIONS

Nu Mark LLC, IPR2016-01303, Ex.1018 U.S. Pat. No. 3,200,819 ("Gilbert"), Jun. 28, 2016.
Nu Mark LLC, IPR2016-01303, Ex.1019 U.S. Pat. No. 6,501,052 ("Cox"), Jun. 28, 2016.
Nu Mark LLC, IPR2016-01303, Ex.1020 U.S. Pat. No. 6,491,233 ("Nichols"), Jun. 28, 2016.
Nu Mark LLC, Petition for Inter Partes Review of U.S. Pat. No. 9,326,548—IPR2016-01641, Paper 1 Petition, Aug. 18, 2016.
Nu Mark LLC, IPR2016-01641, Ex. 1001 U.S. Pat. No. 9,326,548 (the "548 Patent"), Aug. 18, 2016.
Nu Mark LLC, IPR2016-01641, Ex. 1002 File History for U.S. Pat. No. 9,326,548, Aug. 18, 2016.
Nu Mark LLC, IPR2016-01641, Ex. 1003 Declaration of John M. Collins, Ph.D., Aug. 18, 2016.
Nu Mark LLC, IPR2016-01641, Ex. 1004 Curriculum Vitae of Dr. John M. Collins, Aug. 18, 2016.
Nu Mark LLC, IPR2016-01641, Ex. 1005 U.S. Pat. App. Pub. No. 2009/0095311 A1 ("Han 311"), Aug. 18, 2016.
Nu Mark LLC, IPR2016-01641, Ex. 1006 File History for U.S. Appl. No. 13/079,937 (issued as U.S. Pat. No. 8,365,742), Aug. 18, 2016.
Nu Mark LLC, IPR2016-01641, Ex. 1007 Substitute Specification filed in U.S. Appl. No. 13/079,937 (issued as U.S. Pat. No. 8,365,742), Aug. 18, 2016.
Nu Mark LLC, IPR2016-01641, Ex. 1008 U.S. Pat. No. 8,365,742 (the "742 Patent"), Aug. 18, 2016.
Nu Mark LLC, IPR2016-01641, Ex. 1009 U.S. Pat. No. 8,156,944 (the "944 Patent"), Aug. 18, 2016.
Nu Mark LLC, IPR2016-01641, Ex. 1010 File History for U.S. Pat. No. 8,156,944, Aug. 18, 2016.
Nu Mark LLC, IPR2016-01641, Ex. 1011 Institution Decision, *VMR Prods. LLC v. Fontem Holdings 1 B.V.*, IPR2015-000859, Paper 9 (P.T.A.B. Sep. 16, 2015), Aug. 18, 2016.
Nu Mark LLC, IPR2016-01641, Ex. 1012 Rulings on Claims Construction, *Fontem Ventures BV et al. v. Njoy, Inc. et al.*, No. 2:14-cv-01645, Dkt. 65 (C.D. Cal., Jan. 29, 2015), Aug. 18, 2016.
Nu Mark LLC, Petition for Inter Partes Review of U.S. Pat. No. 9,326,548—IPR2017-00204, Paper 2 Petition, Nov. 4, 2016.
Nu Mark LLC, IPR2017-00204, Ex. 1001 U.S. Pat. No. 9,326,548 (the "548 Patent"), Nov. 4, 2016.
Nu Mark LLC, IPR2017-00204, Ex. 1002 File History for U.S. Pat. No. 9,326,548, Nov. 4, 2016.
Nu Mark LLC, IPR2017-00204, Ex. 1003 Declaration of Dr. John M. Collins ("Collins Decl."), Nov. 4, 2016.
Nu Mark LLC, IPR2017-00204, Ex. 1004 WO 2005/099494 to Hon Lik ("Hon 494") (Int'l App. No. PCT/CN2005/000337, which is the PCT application equivalent of CN2719043Y, "Hon 043"), Nov. 4, 2016.
Nu Mark LLC, IPR2017-00204, Ex. 1005 Certified Translation of WO 2005/099494 ("Hon 494"), Nov. 4, 2016.
Nu Mark LLC, IPR2017-00204, Ex. 1006 U.S. Pat. No. 2,057,353 ("Whittemore"), Nov. 4, 2016.
Nu Mark LLC, IPR2017-00204, Ex. 1007 U.S. Pat. No. 5,894,841 ("Voges"), Nov. 4, 2016.
Nu Mark LLC, IPR2017-00204, Ex. 1008 U.S. Pat. No. 6,155,268 ("Takeuchi"), Nov. 4, 2016.
Nu Mark LLC, IPR2017-00204, Ex. 1009 U.S. Pat. No. 4,947,874 ("Brooks"), Nov. 4, 2016.
Nu Mark LLC, IPR2017-00204, Ex. 1010 IPR2013-00387, Final Written Decision, Paper 43, dated Nov. 4, 2016.
Nu Mark LLC, IPR2017-00204, Ex. 1011 IPR2015-00859, Institution Decision, Paper 9, Nov. 4, 2016.
Nu Mark LLC, IPR2017-00204, Ex. 1012 *Fontem Ventures, B.V., et al. v. Njoy, Inc. et al.*, Case 2:14-cv-01645-GW-MRW, Rulings on Claims Construction (DI-65), Nov. 4, 2016.
Nu Mark LLC, IPR2017-00204, Ex. 1013 Random House Webster's College Dictionary, 1226 (1991), Nov. 4, 2016.
Nu Mark LLC, IPR2017-00204, Ex. 1014 U.S. Pat. No. 2,461,664 ("Smith"), Nov. 4, 2016.
Nu Mark LLC, IPR2017-00204, Ex. 1015 U.S. Pat. No. 3,234,357 ("Seuthe"), Nov. 4, 2016.
Nu Mark LLC, IPR2017-00204, Ex. 1016 U.S. Pat. No. 1,084,304 ("Vaughn"), Nov. 4, 2016.
Nu Mark LLC, IPR2017-00204, Ex. 1017 IPR2016-01297, Patent Owner's Preliminary Response, Paper 8, Nov. 4, 2016.
Nu Mark LLC, IPR2017-00204, Ex. 1018 IPR2016-01288, Ex.2009 to Patent Owner's Preliminary Response, Nov. 4, 2016.
Nu Mark LLC, IPR2017-00204, Ex. 1019 IPR2013-00387, Institution Decision, Paper 7, Nov. 4, 2016.
Nu Mark LLC, IPR2017-00204, Ex. 1020 IPR2016-01268, Patent Owner's Preliminary Response, Paper 8, Nov. 4, 2016.
Nu Mark LLC, IPR2017-00204, Ex. 1021 Certified Translation of CN 201018927Y ("Wang"), Nov. 4, 2016.
Nu Mark LLC, IPR2017-00204, Ex. 1022 WIPO Publication No. WO 2007/078273 ("Liu"), Nov. 4, 2016.
Nu Mark LLC, Answer to Complaint and Counterclaims in *Fontem Ventures B.V. v. Nu Mark LLC*, 16-CV-1259, Dkt. 034, Oct. 26, 2016.
Nu Mark LLC, Answer to Complaint in *Fontem Ventures B.V. v. Nu Mark LLC*, 16-CV-2291, Dkt. 025, Jun. 27, 2016.
Nu Mark LLC, First Amended Answer and Counterclaims in *Fontem Ventures B.V. v. Nu Mark LLC*, 16-CV-2291, Dkt. 042, Jul. 28, 2016.
Pan, Fenglin—Request for Invalidation of CN200720148285.9, with English translation.
Pan, Fenglin—Request for Invalidation of CN200920001296.3, with English translation.
Philip Morris Products S.A., Opposition to EP2022349—Additional Observations, Apr. 15, 2016.
Philip Morris Products S.A., Opposition to EP2022349—Affidavit of Huixin Guo, submitted with Additional Observations, Apr. 15, 2016.
Philip Morris Products S.A., Opposition to EP2022349—Additional Observations, Aug. 8, 2016.
Philip Morris Products S.A., Opposition to EP2022349—Additional Observations, Sep. 2, 2016.
Philip Morris Products S.A., Opposition to EP2022349—HP-2015-000027, High Court of Justice Decision Regarding EP(UK)2022349, submitted with Additional Observations, Sep. 2, 2016.
Philip Morris Products S.A., Opposition to EP2022349—HP-2015-000027, Expert Report of Ping Chai, submitted with Additional Observations, Sep. 2, 2016.
Philip Morris Products S.A., Opposition to EP2022349—HP-2015-000027, Exhibit PC.1 to Expert Report of Ping Chai, submitted with Additional Observations, Sep. 2, 2016.
Philip Morris Products S.A., Opposition to EP2022349—HP-2015-000027, Exhibit PC.2 to Expert Report of Ping Chai, submitted with Additional Observations, Sep. 2, 2016.
Philip Morris Products S.A., Opposition to EP2022349—HP-2015-000027, Exhibit PC.3 to Expert Report of Ping Chai, submitted with Additional Observations, Sep. 2, 2016.
Philip Morris Products S. A., Notice and Grounds of Opposition to European Patent No. EP2022349, Apr. 30, 2015.
R.J. Reynolds Vapor Company, Answer to Complaint in *Fontem Holdings B.V. v. R.J. Reynolds Vapor Company*, 16-CV-2286, Dkt. 027, Jun. 27, 2016.
R.J. Reynolds Vapor Company, First Amended Answer to Complaint in *Fontem Holdings B.V. v. R.J. Reynolds Vapor Company*, 16-CV-2286, Dkt. 033, Jul. 25, 2016.
R.J. Reynolds Vapor Company, Answer to Complaint in *Fontem Holdings B.V. v. R.J. Reynolds Vapor Company*, 16-CV-3049, Dkt. 028, Jul. 25, 2016.
R.J. Reynolds Vapor Company, Preliminary Invalidity Contentions served in Middle District of North Carolina, Case No. 16-cv-01255, Mar. 15, 2017.
R.J. Reynolds Vapor Company, Preliminary Invalidity Contentions served in Middle District of North Carolina, Case No. 16-cv-01255, Mar. 15, 2017, Exhibit A ('742 patent).
R.J. Reynolds Vapor Company, Preliminary Invalidity Contentions served in Middle District of North Carolina, Case No. 16-cv-01255, Mar. 15, 2017, Exhibit E ('548 patent).

(56) References Cited

OTHER PUBLICATIONS

R.J. Reynolds Vapor Company, Preliminary Invalidity Contentions served in Middle District of North Carolina, Case No. 16-cv-01255 (for 17-cv-0175), Jul. 31, 2017.
R.J. Reynolds Vapor Company, Preliminary Invalidity Contentions served in Middle District of North Carolina, Case No. 16-cv-01255 (for 17-cv-0175), Jul. 31, 2017, Exhibit H (U.S. Pat. No. 9,456,632).
R.J. Reynolds Vapor Company, Petition for Inter Partes Review of U.S. Pat. No. 9,456,632—IPR2018-00634, Mar. 1, 2018.
R.J. Reynolds Vapor Company, Petition for Inter Partes Review of U.S. Pat. No. 9,456,632—IPR2018-00634, Ex. 1001: U.S. Pat. No. 9,456,632 ("632 patent"), Mar. 1, 2018.
R.J. Reynolds Vapor Company, Petition for Inter Partes Review of U.S. Pat. No. 9,456,632—IPR2018-00634, Ex. 1002: Expert Declaration of Robert Sturges, Ph.D. , Mar. 1, 2018.
R.J. Reynolds Vapor Company, Petition for Inter Partes Review of U.S. Pat. No. 9,456,632—IPR2018-00634, Ex. 1003: U.S. Pat. No. 4,947,874 ("Brooks") , Mar. 1, 2018.
R.J. Reynolds Vapor Company, Petition for Inter Partes Review of U.S. Pat. No. 9,456,632—IPR2018-00634, Ex. 1004: U.S. Pat. No. 2,057,353 ("Whittemore") , Mar. 1, 2018.
R.J. Reynolds Vapor Company, Petition for Inter Partes Review of U.S. Pat. No. 9,456,632—IPR2018-00634, Ex. 1005: U.S. Pat. No. 5,894,841 ("Voges") , Mar. 1, 2018.
R.J. Reynolds Vapor Company, Petition for Inter Partes Review of U.S. Pat. No. 9,456,632—IPR2018-00634, Ex. 1008: U.S. Pat. No. 6,155,268 to Takeuchi, Mar. 1, 2018.
R.J. Reynolds Vapor Company, Petition for Inter Partes Review of U.S. Pat. No. 9,456,632—IPR2018-00634, Ex. 1009: Chinese Pat. No. 2719043Y ("Hon 043") (including certified translation) , Mar. 1, 2018.
R.J. Reynolds Vapor Company, Petition for Inter Partes Review of U.S. Pat. No. 9,456,632—IPR2018-00634, Ex. 1010: U.S. Pat. No. 5,743,251 ("Howell"), Mar. 1, 2018.
R.J. Reynolds Vapor Company, Petition for Inter Partes Review of U.S. Pat. No. 9,456,632—IPR2018-00634, Ex. 1011: U.S. Pat. No. 2,461,664 ("Smith"), Mar. 1, 2018.
R.J. Reynolds Vapor Company, Petition for Inter Partes Review of U.S. Pat. No. 9,456,632—IPR2018-00634, Ex. 1012: U.S. Pat. No. 3,234,357 ("Seuthe"), Mar. 1, 2018.
R.J. Reynolds Vapor Company, Petition for Inter Partes Review of U.S. Pat. No. 9,456,632—IPR2018-00634, Ex. 1013: Contact, Merriam-Webster's Collegiate Dictionary, Merriam-Webster, Inc. (11th ed. 2003), Mar. 1, 2018.
R.J. Reynolds Vapor Company, Petition for Inter Partes Review of U.S. Pat. No. 9,456,632—IPR2018-00634, Ex. 1014: U.S. Pat. Pub. No. 2004/0234916 ("Hale"), Mar. 1, 2018.
R.J. Reynolds Vapor Company, Petition for Inter Partes Review of U.S. Pat. No. 9,456,632—IPR2018-00634, Ex. 1015: U.S. Pat. No. 4,922,901 ("Brooks 901"), Mar. 1, 2018.
R.J. Reynolds Vapor Company, Petition for Inter Partes Review of U.S. Pat. No. 9,456,632—IPR2018-00634, Ex. 1016: U.S. Pat. No. 1,084,304 ("Vaughn"), Mar. 1, 2018.
R.J. Reynolds Vapor Company, Petition for Inter Partes Review of U.S. Pat. No. 9,456,632—IPR2018-00634, Ex. 1017: Institution Decision dated Feb. 7, 2017 (Paper 9), *R.J. Reynolds Vapor Co.* v. *Fontem Holdings 1 B.V.*, IPR2016-01532 (P.T.A.B., petition filed Aug. 5, 2016), Mar. 1, 2018.
R.J. Reynolds Vapor Company, Petition for Inter Partes Review of U.S. Pat. No. 9,456,632—IPR2018-00634, Ex. 1018: Institution Decision dated Mar. 6, 2017 (Paper 9), *R.J. Reynolds Vapor Co.* v. *Fontem Holdings 1 B.V.*, IPR2016-01691 (P.T.A.B., petition filed Aug. 30, 2016), Mar. 1, 2018.
R.J. Reynolds Vapor Company, Petition for Inter Partes Review of U.S. Pat. No. 9,456,632—IPR2018-00634, Ex. 1019: U.S. Pat. No. 3,292,635 ("Kolodny"), Mar. 1, 2018.
R.J. Reynolds Vapor Company, Petition for Inter Partes Review of U.S. Pat. No. 9,456,632—IPR2018-00634, Ex. 1020: U.S. Pat. No. 3,685,521 ("Dock"), Mar. 1, 2018.
R.J. Reynolds Vapor Company, Petition for Inter Partes Review of U.S. Pat. No. 9,456,632—IPR2018-00634, Ex. 1022: Institution Decision dated Feb. 5, 2018 (Paper 9), *Cascades Canada ULC* v. *SCA Hygiene Prods AB*, IPR2017-01921 (P.T.A.B., petition filed Aug. 7, 2017), Mar. 1, 2018.
R.J. Reynolds Vapor Company, Petition for Inter Partes Review of U.S. Pat. No. 9,456,632—IPR2018-00634, Ex. 1023: Institution Decision dated Jan. 19, 2018 (Paper 9), *Donghee America, Inc.* v. *Plastic Omnium Advanced Innovation and Research*, IPR2017-01654 (P.T.A.B., petition filed Jun. 21, 2017), Mar. 1, 2018.
R.J. Reynolds Vapor Company, Petition for Inter Partes Review of U.S. Pat. No. 9,456,632—IPR2018-00634, Ex. 1024: Institution Decision dated May 18, 2017 (Paper 9), *Limelight Networks, Inc.* v. *Mass. Inst. of Tech.*, IPR2017-00249 (P.T.A.B., petition filed Nov. 11, 2016), Mar. 1, 2018.
R.J. Reynolds Vapor Company, Petition for Inter Partes Review of U.S. Pat. No. 9,456,632—IPR2018-00634, Ex. 1025: Institution Decision dated Jul. 15, 2015 (Paper 10), *Microsoft Corp.* v. *Parallel Networks Licensing, LLC*, IPR2015-00483 (P.T.A.B., petition filed Dec. 23, 2014), Mar. 1, 2018.
R.J. Reynolds Vapor Company, Petition for Inter Partes Review of U.S. Pat. No. 9,456,632—IPR2018-00634, Ex. 1026: Institution Decision dated Mar. 13, 2013 (Paper 19), *Micron Tech., Inc.* v. *Bd. of Trs. of the Univ. of Ill.*, IPR2013-00005 (P.T.A.B., petition filed Oct. 2, 2012), Mar. 1, 2018.
R.J. Reynolds Vapor Company, Petition for Inter Partes Review of U.S. Pat. No. 9,456,632—IPR2018-00634, Ex. 1027: Institution Decision dated Jan. 24, 2013 (Paper 18), *Macauto U.S.A.* v. *Bos GMBH & KG*, IPR2012-00004 (P.T.A.B., petition filed Sep. 16, 2012), Mar. 1, 2018.
R.J. Reynolds Vapor Company, Petition for Inter Partes Review of U.S. Pat. No. 9,456,632—IPR2018-00634, Ex. 1028: Institution Decision dated Feb. 6, 2018 (Paper 8), *Samsung Elecs. Am.* v. *Uniloc*, IPR2017-01801 (P.T.A.B., petition filed Jul. 20, 2017), Mar. 1, 2018.
R.J. Reynolds Vapor Company, Petition for Inter Partes Review of U.S. Pat. No. 9,456,632—IPR2018-00634, Ex. 1029: Institution Decision dated Jan. 4, 2017 (Paper 11), *R.J. Reynolds Vapor Company* v. *Fontem Holdings 1 B.V.*, IPR2016-01270 (P.T.A.B., petition filed Jul. 2, 2016), Mar. 1, 2018.
R.J. Reynolds Vapor Company, Petition for Inter Partes Review of U.S. Pat. No. 9,456,632—IPR2018-00634, Ex. 1030: U.S. Pat. Pub. No. 2005/0016550 ("Katase"), Mar. 1, 2018.
R.J. Reynolds Vapor Company, Petition for Inter Partes Review of U.S. Pat. No. 9,456,632—IPR2018-00634, Ex. 1033: U.S. Pat. No. 4,941,486 ("Dube"), Mar. 1, 2018.
R.J. Reynolds Vapor Company, Petition for Inter Partes Review of U.S. Pat. No. 9,456,632—IPR2018-00634, Ex. 1034: U.S. Pat. No. 7,337,782 ("Thompson"), Mar. 1, 2018.
R.J. Reynolds Vapor Company, Petition for Inter Partes Review of U.S. Pat. No. 9,456,632—IPR2018-00634, Ex. 1035: Declaration of Kyle E. Yarberry, Mar. 1, 2018.
R.J. Reynolds Vapor Company, Petition for Inter Partes Review of U.S. Pat. No. 9,456,632—IPR2018-00634, Ex. 1036: WO00/28843 ("Pienemann"), Mar. 1, 2018.
R.J. Reynolds Vapor Company, Petition for Inter Partes Review of U.S. Pat. No. 9,456,632—IPR2018-00634, Ex. 1037: Certified Translation of WO00/28843, Mar. 1, 2018.
R.J. Reynolds Vapor Company, Petition for Inter Partes Review of U.S. Pat. No. 8,365,742—IPR2016-01268, Paper 2, Jul. 2, 2016.
R.J. Reynolds Vapor Company, IPR2016-01268, Ex. 1001 U.S. Pat. No. 8,365,742 to Lik Hon, Jul. 2, 2016.
R.J. Reynolds Vapor Company, IPR2016-01268, Ex. 1002 Chinese Pat. No. 2719043Y to Lik Hon, Jul. 2, 2016.
R.J. Reynolds Vapor Company, IPR2016-01268, Ex. 1003 Certified English translation of Chinese Pat. No. 2719043Y to Lik Hon, Jul. 2, 2016.
R.J. Reynolds Vapor Company, IPR2016-01268, Ex. 1004 U.S. Pat. No. 2,057,353 to C. L. Whittemore, Jr, Jul. 2, 2016.
R.J. Reynolds Vapor Company, IPR2016-01268, Ex. 1005 Application Data Sheet of Apr. 5, 2011 Filed in U.S. Appl. No. 13/079,937, Jul. 2, 2016.

(56) References Cited

OTHER PUBLICATIONS

R.J. Reynolds Vapor Company, IPR2016-01268, Ex. 1006 Preliminary Amendment dated Apr. 5, 2011 Filed in U.S. Appl. No. 13/079,937, Jul. 2, 2016.
R.J. Reynolds Vapor Company, IPR2016-01268, Ex. 1007 Non-Final Office Action dated Jul. 19, 2012 in U.S. Appl. No. 13/079,937, Jul. 2, 2016.
R.J. Reynolds Vapor Company, IPR2016-01268, Ex. 1008 Amendment dated Aug. 3, 2012 in U.S. Appl. No. 13/079,937, Jul. 2, 2016.
R.J. Reynolds Vapor Company, IPR2016-01268, Ex. 1009 PCT Pub. No. WO2007131449, Jul. 2, 2016.
R.J. Reynolds Vapor Company, IPR2016-01268, Ex. 1010 English translation of PCT Pub. No. WO2007131449, Jul. 2, 2016.
R.J. Reynolds Vapor Company, IPR2016-01268, Ex. 1011 Board's Decision Denying Institution in IPR2015-00859, Jul. 2, 2016.
R.J. Reynolds Vapor Company, IPR2016-01268, Ex. 1012 Patent Owner's Preliminary Response to Petition for IPR of U.S. Pat. No. 8,365,742 in IPR2015-00859, Jul. 2, 2016.
R.J. Reynolds Vapor Company, IPR2016-01268, Ex. 1013 Petition for IPR of U.S. Pat. No. 8,365,742 in IPR2015-00859, Jul. 2, 2016.
R.J. Reynolds Vapor Company, IPR2016-01268, Ex. 1014 Board's Order Dismissing Petition in IPR2015-01587, Jul. 2, 2016.
R.J. Reynolds Vapor Company, IPR2016-01268, Ex. 1015 Declaration of Dr. Robert Sturges, Jul. 2, 2016.
R.J. Reynolds Vapor Company, IPR2016-01268, Ex. 1016 Rohsenow, "Heat, Mass, and Momentum Transfer", Jul. 2, 2016.
R.J. Reynolds Vapor Company, IPR2016-01268, Ex. 1017 WO 2005/099494, which is the PCT application equivalent of CN2719043Y to Hon ("Hon '494"), Jul. 2, 2016.
R.J. Reynolds Vapor Company, IPR2016-01268, Ex. 1018 Certified English translation of WO 2005/099494 pursuant to 37 C.F.R. 42.63(b), Jul. 2, 2016.
R.J. Reynolds Vapor Company, IPR2016-01532, Paper 1 Petition, Aug. 5, 2016.
R.J. Reynolds Vapor Company, Petition for Inter Partes Review of U.S. Pat. No. 8,365,742—IPR2016-01532, Ex. 1001 U.S. Pat. No. 8,365,742 to Lik Hon, Aug. 5, 2016.
R.J. Reynolds Vapor Company, IPR2016-01532, Ex. 1002 U.S. Pat. Pub. No. 2009/0095311 to Li Han, Aug. 5, 2016.
R.J. Reynolds Vapor Company, IPR2016-01532, Ex. 1003 Chinese Pat. Appl. No. 200620090805.0, Aug. 5, 2016.
R.J. Reynolds Vapor Company, IPR2016-01532, Ex. 1004 English translation of Chinese Pat. Appl. No. 200620090805.0, Aug. 5, 2016.
R.J. Reynolds Vapor Company, IPR2016-01532, Ex. 1005 PCT publication corresponding to PCT/CN2007/001575, Aug. 5, 2016.
R.J. Reynolds Vapor Company, IPR2016-01532, Ex. 1006 English translation of PCT '575, Aug. 5, 2016.
R.J. Reynolds Vapor Company, IPR2016-01532, Ex. 1007 PCT publication corresponding to PCT/CN2007/001576, Aug. 5, 2016.
R.J. Reynolds Vapor Company, IPR2016-01532, Ex. 1008 English translation of PCT '576, Aug. 5, 2016.
R.J. Reynolds Vapor Company, IPR2016-01532, Ex. 1009 U.S. Appl. No. 12/226,818, filed Oct. 29, 2008, including English translation of the PCT publication (also included as Ex. 1006), Application Data Sheet, and Preliminary Amendment, dated Aug. 5, 2016.
R.J. Reynolds Vapor Company, IPR2016-01532, Ex. 1010 U.S. Appl. No. 13/079,937 with Preliminary Amendment filed Apr. 5, 2011, dated Aug. 5, 2016.
R.J. Reynolds Vapor Company, IPR2016-01532, Ex. 1011 Amendment with Substitute Specification Filed in U.S. Appl. No. 13/079,937 on Aug. 7, 2012, dated Aug. 5, 2016.
R.J. Reynolds Vapor Company, IPR2016-01532, Ex. 1012 Declaration of Dr. Robert Sturges, Aug. 5, 2016.
R.J. Reynolds Vapor Company, IPR2016-01532, Ex. 1013 Board's Decision Denying Institution in IPR2015-00859, Aug. 5, 2016.
R.J. Reynolds Vapor Company, IPR2016-01532, Ex. 1014 Rulings on Claims Construction, *Fontem Ventures, B.V. et al. v. Njoy, Inc. et al.*, No. 2:14-cv-01645 (C.D. Cal., filed Mar. 5, 2014), Aug. 5, 2016.
R.J. Reynolds Vapor Company, IPR2016-01532, Ex. 1015 U.S. Pat. No. 8,156,944, Aug. 5, 2016.
R.J. Reynolds Vapor Company, IPR2016-01532, Ex. 1016 Complaint, *Fontem Ventures B.V. et al. v. R.J. Reynolds Vapor Company*, No. 2:16-cv-02286 (C.D. Cal., filed Apr. 4, 2016), Aug. 5, 2016.
R.J. Reynolds Vapor Company., Petition for Inter Partes Review of U.S. Pat. No. 9,326,548—IPR2016-01691, Paper 2 Petition, Aug. 30, 2016.
R.J. Reynolds Vapor Company, IPR2016-01691, Ex. 1001 U.S. Pat. No. 9,326,548 to Lik Hon, Aug. 30, 2016.
R.J. Reynolds Vapor Company, IPR2016-01691, Ex. 1002 U.S. Pat. Pub. No. 2009/0095311 to Li Han, Aug. 30, 2016.
R.J. Reynolds Vapor Company, IPR2016-01691, Ex. 1003 Chinese Pat. Appl. No. 200620090805.0, Aug. 30, 2016.
R.J. Reynolds Vapor Company, IPR2016-01691, Ex. 1004 English translation of Chinese Pat. Appl. No. 200620090805, Aug. 30, 2016.
R.J. Reynolds Vapor Company, IPR2016-01691, Ex. 1005 PCT publication corresponding to PCT/CN2007/001575, Aug. 30, 2016.
R.J. Reynolds Vapor Company, IPR2016-01691, Ex. 1006 English translation of PCT '575, Aug. 30, 2016.
R.J. Reynolds Vapor Company, IPR2016-01691, Ex. 1007 PCT publication corresponding to PCT/CN2007/001576, Aug. 30, 2016.
R.J. Reynolds Vapor Company, IPR2016-01691, Ex. 1008 English translation of PCT '576, Aug. 30, 2016.
R.J. Reynolds Vapor Company, IPR2016-01691, Ex. 1009 U.S. Appl. No. 12/226,818, filed Oct. 29, 2008, including English translation of the PCT publication (also included as Ex. 1006), Application Data Sheet, and Preliminary Amendment, dated Aug. 30, 2016.
R.J. Reynolds Vapor Company, IPR2016-01691, Ex. 1010 U.S. Appl. No. 13/079,937 with Preliminary Amendment filed Apr. 5, 2011, dated Aug. 30, 2016.
R.J. Reynolds Vapor Company, IPR2016-01691, Ex. 1011 Amendment with Substitute Specification Filed in U.S. Appl. No. 13/079,937 on Aug. 7, 2012, dated Aug. 30, 2016.
R.J. Reynolds Vapor Company, IPR2016-01691, Ex. 1012 U.S. Appl. No. 13/740,011, filed Jan. 11, 2013, Aug. 30, 2016.
R.J. Reynolds Vapor Company, IPR2016-01691, Ex. 1013 U.S. Appl. No. 14/244,376, filed Apr. 3, 20, Aug. 30, 2016.
R.J. Reynolds Vapor Company, IPR2016-01691, Ex. 1014 Amendment Filed in U.S. Appl. No. 14/244,376 on Nov. 20, 2015, dated Aug. 30, 2016.
R.J. Reynolds Vapor Company, IPR2016-01691, Ex. 1015 Declaration of Dr. Robert Sturges, Aug. 30, 2016.
R.J. Reynolds Vapor Company, IPR2016-01691, Ex. 1016 Board's Decision Denying Institution in IPR2015-00859, Aug. 30, 2016.
R.J. Reynolds Vapor Company, IPR2016-01691, Ex. 1017 Rulings on Claims Construction, *Fontem Ventures, B.V. et al. v. Njoy, Inc. et al.*, No. 2:14-cv-01645 (C.D. Cal., filed Mar. 5, 2014), Aug. 30, 2016.
R.J. Reynolds Vapor Company, IPR2016-01691, Ex. 1018 U.S. Pat. No. 8,156,944, Aug. 30, 2016.
R.J. Reynolds Vapor Company, IPR2016-01691, Ex. 1019 Complaint, *Fontem Ventures B.V. et al. v. R.J. Reynolds Vapor Company*, No. 2:16-cv-03049 (C.D. Cal., filed May 3, 2016), Aug. 30, 2016.
R.J. Reynolds Vapor Company, Petition for Inter Partes Review of U.S. Pat. No. 9,326,548—IPR2016-01692, Paper 2 Petition, Aug. 30, 2016.
R.J. Reynolds Vapor Company, IPR2016-01692, Ex. 1001 U.S. Pat. No. 9,326,548 to Lik Hon, Aug. 30, 2016.
R.J. Reynolds Vapor Company, IPR2016-01692, Ex. 1002 Chinese Pat. No. 2719043Y to Lik Hon, Aug. 30, 2016.
R.J. Reynolds Vapor Company, IPR2016-01692, Ex. 1003 Certified English translation of Chinese Pat. No. 2719043Y to Lik Hon, Aug. 30, 2016.
R.J. Reynolds Vapor Company, IPR2016-01692, Ex. 1004 U.S. Pat. No. 2,057,353 to C. L. Whittemore, Jr, Aug. 30, 2016.
R.J. Reynolds Vapor Company, IPR2016-01692, Ex. 1005 WO 2005/099494, which is the PCT application equivalent of Hon (CN 2719043Y) ("Hon '494"), Aug. 30, 2016.
R.J. Reynolds Vapor Company, IPR2016-01692, Ex. 1006 Certified English translation of WO 2005/099494 pursuant to 37 C.F.R. 42.63(b), Aug. 30, 2016.

(56) References Cited

OTHER PUBLICATIONS

R.J. Reynolds Vapor Company, IPR2016-01692, Ex. 1007 Application Data Sheet and Specification of U.S. Pat. Appl. No. 14/244,376, filed Apr. 3, 2014, Aug. 30, 2016.
R.J. Reynolds Vapor Company, IPR2016-01692, Ex. 1008 Non-Final Office Action dated Sep. 4, 2014 in U.S. Appl. No. 14/244,376, Aug. 30, 2016.
R.J. Reynolds Vapor Company, IPR2016-01692, Ex. 1009 Compilation of prosecution papers filed in U.S. Appl. No. 14/244,376, Aug. 30, 2016.
R.J. Reynolds Vapor Company, IPR2016-01692, Ex. 1010 Non-Final Office Action dated Aug. 20, 2015 in U.S. Appl. No. 14/244,376, Aug. 30, 2016.
R.J. Reynolds Vapor Company, IPR2016-01692, Ex. 1011 Amendment dated Nov. 20, 2015 in U.S. Appl. No. 14/244,376, Aug. 30, 2016.
R.J. Reynolds Vapor Company, IPR2016-01692, Ex. 1012 Notice of Allowance dated Mar. 15, 2016 in U.S. Appl. No. 14/244,376, Aug. 30, 2016.
R.J. Reynolds Vapor Company, IPR2016-01692, Ex. 1013 Board's Decision Denying Institution in IPR2015-00859, Aug. 30, 2016.
R.J. Reynolds Vapor Company, IPR2016-01692, Ex. 1014 Board's Order Dismissing Petition IPR2015-01587, Aug. 30, 2016.
R.J. Reynolds Vapor Company, IPR2016-01692, Ex. 1015 Declaration of Dr. Robert Sturges, Aug. 30, 2016.
R.J. Reynolds Vapor Company, IPR2016-01692, Ex. 1016 Rohsenow, "Heat, Mass, and Momentum Transfer", Aug. 30, 2016.
R.J. Reynolds Vapor Company, IPR2016-01692, Ex. 1017 Merriam-Webster Definition of "Set", Aug. 30, 2016.
R.J. Reynolds Vapor Company, IPR2016-01692, Ex. 1018 U.S. Pat. No. 6,155,268 to Takeuchi, Aug. 30, 2016.
R.J. Reynolds Vapor Company, IPR2016-01692, Ex. 1019 U.S. Pat. No. 4,947,874 to Brooks et al., Aug. 30, 2016.
R.J. Reynolds Vapor Company, IPR2016-01692, Ex. 1020 U.S. Pat. No. 4,629,665 to Matsuo, Aug. 30, 2016.
R.J. Reynolds Vapor Company, IPR2016-01692, Ex. 1021 U.S. Pat. No. 5,894,841 to Voges, Aug. 30, 2016.
R.J. Reynolds Vapor Company, IPR2016-01692, Ex. 1022 U.S. Pat. Pub. No. 2005/0016550 to Katase, Aug. 30, 2016.
R.J. Reynolds Vapor Company, IPR2016-01692, Ex. 1023 U.S. Pat. No. 5,703,633 to Gehrer et al., Aug. 30, 2016.
R.J. Reynolds Vapor Company, IPR2016-01692, Ex. 1024 IPR2014-01300, Paper No. 8, Aug. 30, 2016.
United States Patent and Trademark Office, Patent Trial and Appeal Board, *R.J. Reynolds Vapor Co.* v. *Fontem Holdings 1 B.V.*, IPR2016-01268, Paper 10—Decision Instituting Inter Partes Review, Jan. 3, 2017.
Sottera, Inc., *Ruyan* v. *Smoking Everywhere et al.* CV11-0367 Invalidity Contentions Exhibit 7 (Claim 20 Claim Chart), Apr. 12, 2012.
Sottera, Inc., *Ruyan* v. *Smoking Everywhere et al.* CV11-0367 Invalidity Contentions Exhibit 8 (Claim 24 Claim Chart), Apr. 12, 2012.
Sottera, Inc., *Ruyan* v. *Smoking Everywhere et al.* CV11-0367 Invalidity Contentions, Apr. 12, 2012.
State Intellectual Property Office, P.R. China, English translation of Written Opinion for PCT/CN07/001576, dated Aug. 3, 2007.
State Intellectual Property Office, P.R. China, International Search Report for PCT/CN04/000182, dated Jun. 10, 2004.
State Intellectual Property Office, P.R. China, International Search Report for PCT/CN05/000337, dated Jul. 14, 2005.
State Intellectual Property Office, P.R. China, Decision on Patent Invalidation Petition for CN200720148285.9, with English translation, Oct. 31, 2014.
State Intellectual Property Office, P.R. China, English Translation of Written Opinion for PCT/CN07/001575, dated Jul. 20, 2007.
State Intellectual Property Office, P.R. China, International Search Report and Written Opinion for PCT/CN10/073613, dated Aug. 26, 2010.
State Intellectual Property Office, P.R. China, International Search Report for PCT/CN07/001575, dated Aug. 16, 2007.
State Intellectual Property Office, P.R. China, International Search Report for PCT/CN07/001576, dated Aug. 16, 2007.
State Intellectual Property Office, P.R. China, International Search Report for PCT/CN10/000125, dated Apr. 1, 2010.
State Intellectual Property Office, P.R. China, Office Action for CN201080016105.6, dated Aug. 30, 2013, with English translation.
State Intellectual Property Office, P.R. China, Search Report for Utility Model Patent ZL 200620090805.0, dated Nov. 18, 2008.
Taiwan Patent Office, Official Letter for TW093111573, Apr. 24, 2009.
TechPowerUp "What is a MOSFET, what does it look like and how does it work?" Dated May 24, 2004; 3 pgs. printed from Internet Jun. 4, 2011.
Ten Motives Limited, Notice and Grounds of Opposition to European Patent No. EP2022349, Apr. 27, 2015.
Ukraine Patent Office, Examination Report for UA200511258, dated Feb. 4, 2009.
United States Patent and Trademark Office, Patent Trial and Appeal Board, *VMR Products LLC* v. *Fontem Holdings 1 B.V.*, IPR2015-00859, Paper 9—Decision Denying Institution of Inter Partes Review, Sep. 16, 2015.
United States Patent and Trademark Office Before the Patent Trial and Appeal Board, Inter Partes Review Institution Decision in IPR2013-00387, Paper 7, Dec. 30, 2013.
United States Patent and Trademark Office, Final Office Action for U.S. Appl. No. 14/244,376, dated Apr. 29, 2015, 7 pgs.
United States Patent and Trademark Office, Final Written Decision, *C.B. Distributors, Inc and DR Distributors, LLC* v. *Fontem Holdings 1 B.V.*, Patent No. 8m156,944 B2, entered Dec. 24, 2014.
United States Patent and Trademark Office, Non-Final Office Action for U.S. Appl. No. 13/740,011, dated Jan. 29, 2015.
United States Patent and Trademark Office, Non-Final Office Action for U.S. Appl. No. 13/740,011, dated Jan. 15, 2016, 8 pgs.
United States Patent and Trademark Office, Non-Final Office Action for U.S. Appl. No. 14/244,376, dated Aug. 20, 2015, 9 pgs.
United States Patent and Trademark Office, Non-Final Office Action for U.S. Appl. No. 14/244,376, dated Sep. 4, 2014, 6 pgs.
United States Patent and Trademark Office, Non-Final Office Action for U.S. Appl. No. 15/167,659, dated Oct. 14, 2016, 9 pgs.
United States Patent and Trademark Office, Office Action for U.S. Appl. No. 12/226,818, dated Apr. 12, 2011, 9 pages.
United States Patent and Trademark Office, Office Action for U.S. Appl. No. 13/079,937, dated Jul. 19, 2012.
United States Patent and Trademark Office, Office Action for Inter Partes Reexamination U.S. Appl. No. 95/002,235, dated Mar. 14, 2018, 75 pgs.
United States Patent and Trademark Office, Office Action in Inter Partes Reexamination U.S. Appl. No. 95/002,235, dated Nov. 27, 2012.
U.S. District Court, Central District of California, Western Division, Defendant Njoy, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 1 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 3 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 4 to Defendants' Motion for Leave

(56) References Cited

OTHER PUBLICATIONS to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 5 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Memorandum of Points and Authorities in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy. Inc.'s production documents VLACHOS 0000061-72; Consolidated Case No. CV 14-01645 GW (MRW) and related consolidated cases.
U.S. District Court, Central District of California, Western Division, Defendant Njoy. Inc.'s Reply Brief in Support of Defendants' Motion for Leave to Amend Invalidity Contentions dated Jul. 13, 2015 and filed in Consolidated Case No. CV 14-01645 GW (MRW) and related consolidated cases.
VMR Products LLC, Petition for Inter Partes Review of U.S. Pat. No. 8,365,742—IPR2015-00859, Mar. 10, 2015.
VMR Products LLC, IPR2015-00859, Ex. 1001, U.S. Pat. No. 8,265,742, Mar. 10, 2015.
VMR Products LLC, IPR2015-00859, Ex. 1002, Buckner Declaration, Mar. 10, 2015.
VMR Products LLC, IPR2015-00859, Ex. 1003, Buckner CV, Mar. 10, 2015.
VMR Products LLC, IPR2015-00859, Ex. 1004, CN2719043, Mar. 10, 2015.
VMR Products LLC, IPR2015-00859, Ex. 1005, CN2719043—Certified Translation, Mar. 10, 2015.
VMR Products LLC, IPR2015-00859, Ex. 1006, WO2005099494, Mar. 10, 2015.
VMR Products LLC, IPR2015-00859, Ex. 1007, WO2005099494—Certified Translation, Mar. 10, 2015.
VMR Products LLC, IPR2015-00859, Ex. 1008, CA2562581, Mar. 10, 2015.
VMR Products LLC, IPR2015-00859, Ex. 1009, US20070267031, Mar. 10, 2015.
VMR Products LLC, IPR2015-00859, Ex. 1010, EP0845220, Mar. 10, 2015.
VMR Products LLC, IPR2015-00859, Ex. 1011, U.S. Pat. No. 5,144,962, Mar. 10, 2015.
VMR Products LLC, IPR2015-00859, Ex. 1012, WO2003034847, Mar. 10, 2015.
VMR Products LLC, IPR2015-00859, Ex. 1013, U.S. Pat. No. 2,057,353, Mar. 10, 2015.
VMR Products LLC, IPR2015-00859, Ex. 1014, CV14-1645 Rulings on Claims (litigation proceedings), Mar. 10, 2015.
VMR Products LLC, IPR2015-00859, Ex. 1015, WO2007131449, Mar. 10, 2015.
VMR Products LLC, IPR2015-00859, Ex. 1016, 742 Prosecution History, Preliminary Amendment, dated Mar. 10, 2015.
VMR Products LLC, IPR2015-00859, Ex. 1017, 742 Prosecution History, Non-final Office Action, dated Jul. 19, 2012, Mar. 10, 2015.
VMR Products LLC, IPR2015-00859, Ex. 1018, 742 Prosecution History, Amendment, dated Mar. 10, 2015.
VMR Products LLC, IPR2015-00859, Ex. 1019, 742 Prosecution History, Supplemental Amendment, dated Mar. 10, 2015.
VMR Products LLC, IPR2015-00859, Ex. 1020, 742 Prosecution History, Examiner Interview Summary, dated Mar. 10, 2015.
VMR Products LLC, IPR2015-00859, Ex. 1021, 742 Prosecution History, Notice of Allowance, dated Mar. 10, 2015.
VMR Products LLC, IPR2015-00859, Ex. 1022, 742 Prosecution History, Certificate of Correction, Mar. 10, 2015.

VMR Products LLC, IPR2015-00859, Ex. 1023, Decision—Institution of Inter Partes Review in IPR2013-00387, Paper 7, Mar. 10, 2015.
Wkipedia Entry "Heating Element", Jul. 23, 2007 (D10 of Joyetech EP Opposition above).
*Fontem Ventures B. V.* v. *R.J. Reynolds Vapor Company*, U.S. District Court for the Middle District of North Carolina, Case No. 1:16-cv-01255-CCE-JEP, Dkt. No. 148, Claim Construction Order, Mar. 12, 2018, 8 pages.
*Fontem Ventures B.V.* v. *Njoy, Inc.*, U.S. District Court for the Central District of California, Case 2:14-cv-01645-GW-MRW, Dkt. No. 65, Rulings on Claims Construction, Jan. 29, 2015, 28 pages.
*Fontem Ventures B.V.* v. *Njoy, Inc.*, U.S. District Court for the Central District of California, Case No. Cv 14-1645-GW(MRWx), Dkt. No. 133, Order regarding Markman Hearing/Claim Construction, May 7, 2015, 16 pages.
IP Office India, Application No. IN3528/DELNP/2008, Decision of Refusal, dated Jul. 18, 2017.
USPTO, U.S. Appl. No. 15/167,690, Non-Final Office Action, dated Feb. 25, 2019.
USPTO, U.S. Appl. No. 15/996,969, Non-Final Office Action, dated Mar. 7, 2019.
USPTO, Inter Partes Reexamination U.S. Appl. No. 95/002,235, U.S. Pat. No. 8,156,944, Inter Partes Reexamination Certificate, dated Jan. 23, 2019.
USPTO PTAB, Inter Partes Review Certificate for IPR2013-00387, U.S. Pat. No. 8,156,944. Date Issued: Nov. 16, 2018. 2 pages.
USPTO, U.S. Appl. No. 15/167,690, Nonfinal Office Action dated Sep. 4, 2019.
USPTO, U.S. Appl. No. 15/996,969, Nonfinal Office Action dated Sep. 13, 2019.
USPTO, Final Office Action for U.S. Appl. No. 15/996,969 dated Jan. 10, 2020. 14 pages.
Adares Patent—Und Rechtsanwalte Reininger & Partner GmbH, Opposition to European Patent No. EP2789250, Sep. 26, 2019.
Joyetech Deutschland GmbH, Opposition to European Patent No. EP2789250, Sep. 26, 2019.
Philip Morris Products S.A., Opposition to European Patent No. EP2789250, Sep. 26, 2019.
Joyetech Deutschland GmbH, Opposition to European Patent No. EP3061359, Jul. 3, 2019.
Lang & Tomerius, Opposition to European Patent No. EP3061359, Jul. 3, 2019.
Philip Morris Products S.A., Opposition to European Patent No. EP3061359, Jul. 3, 2019.
USPTO, U.S. Appl. No. 15/167,690, Final Office Action, dated Apr. 1, 2020, 29 pages.
EPO, Summons to attend oral proceedings for European Patent No. 2022349. Mail Date: Aug. 13, 2018. 12 pages.
Joyetech Deutschland GMBH, Opposition to EP2878215, Additional Observations. Mail Date: Mar. 22, 2019. 8 pages.
Philip Morris Products S.A., Opposition to EP2878215, Additional Observations. Mail Date: Mar. 25, 2019. 24 pages.
EPO, Patent Owner Request of Request for Revocation of Patent for European Patent No. 2878215 filed May 10, 2019. 3 pages.
EPO, Decision revoking European Patent No. 2878215. Mail Date: Jul. 10, 2019. 6 pages.
EPO, Appeal Board Communication for European Patent No. 2022349. Mail Date: Dec. 13, 2019. 8 pages.
EPO, Opposition of EP2789250 (Application No. 14155503.7) Provisional Opinion and Summons to Attend Oral Proceedings, Jul. 23, 2020.
EPO, Opposition of EP3061359 (Application No. 16158159.0) Provisional Opinion and Summons to Attend Oral Proceedings, Jul. 27, 2020
USPTO, U.S. Appl. No. 15/167,690, Advisory Action, dated Jun. 23, 2020.
USPTO, U.S. Appl. No. 16/846,189, Nonfinal Office Action, dated Jul. 22, 2020, 18 pages.
USPTO, U.S. Appl. No. 16/846,189, Final Office Action, dated Oct. 28, 2020, 27 pages.

\* cited by examiner

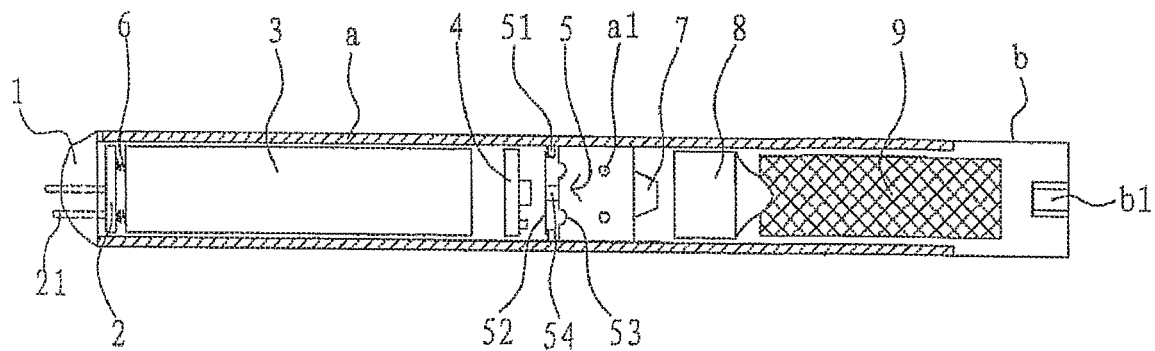
Figure 1
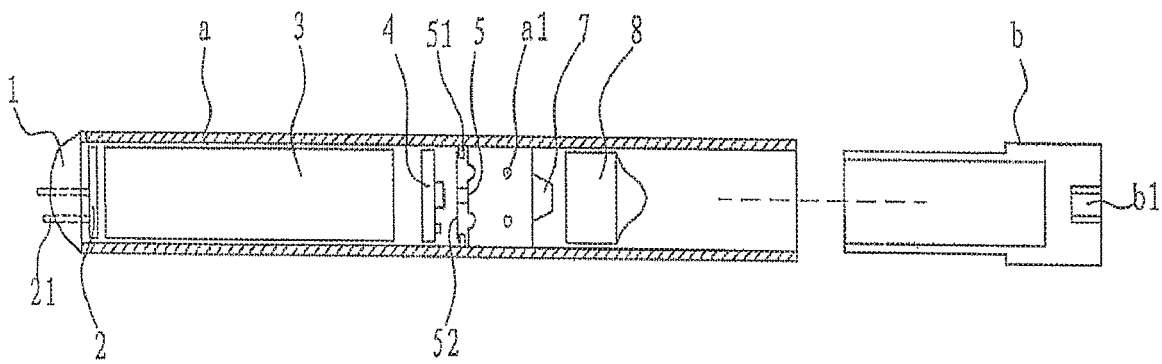
Figure 2
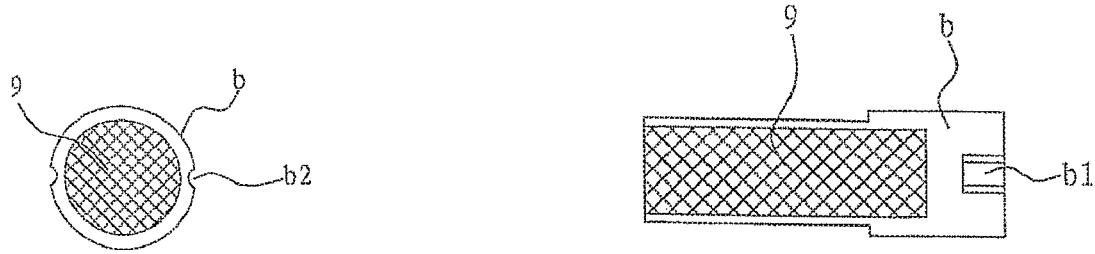
Figure 3
Figure 4

ELECTRONIC CIGARETTE

CROSS-REFERENCE TO RELATED APPLICATIONS

This application is a continuation of U.S. patent application Ser. No. 15/167,690, filed May 27, 2016, which is a continuation of U.S. patent application Ser. No. 13/740,011, filed Jan. 11, 2013 and now issued as U.S. Pat. No. 9,456,632, which is a continuation of U.S. patent application Ser. No. 13/079,937, filed Apr. 5, 2011 and now issued as U.S. Pat. No. 8,365,742, which is a divisional of U.S. patent application Ser. No. 12/226,818, filed Oct. 29, 2008 and now issued as U.S. Pat. No. 8,156,944, which is a 371 national filing of International Application No. PCTCN2007/001575, filed May 15, 2007, which claims priority to Chinese Patent Application No. 200620090805.0, filed May 16, 2006. All these applications are incorporated herein by reference in their entirety.

BACKGROUND ART

Smoking causes serious respiratory system diseases and cancer, though it is hard to persuade the smokers to completely quit smoking.

Nicotine is the effective ingredient in cigarettes. Nicotine acts on the receptor of the central nervous system.

Nicotine is a micromolecular alkaloid, which is basically harmless to human bodies at a small dosage. Plus, its half life period is extremely short in blood. Tar is the major harmful substance in tobacco. Tobacco tar comprises several thousands of ingredients, dozens of which are carcinogenic substances.

To provide cigarette substitutes that contain nicotine but not harmful tar, many products have been used. These products are not as harmful as tar, but are absorbed very slowly. As a result, smokers can't be satisfied in full. In addition, the smokers are deprived of the "smoking" habit.

The electronic cigarettes currently available on the market may resolve the above-mentioned issue, though they are complicated in structure, they don't provide the ideal aerosol effects, and their atomizing efficiency is not high.

SUMMARY OF INVENTION

To overcome the above-mentioned disadvantages, an aerosol electronic cigarette includes a battery assembly, an atomizer assembly and a bottle assembly. The battery assembly connects with the atomizer assembly and both are located in a housing. The bottle assembly is located in one end of the housing and fits with the atomizer assembly.

The battery assembly may include the battery, an operating indicator, electronic circuit board, and airflow sensor, which are connected with the battery, and with the signal output of the airflow sensor connected to the electronic circuit board.

A component for liquid storage of the cigarette bottle assembly stores the nicotine liquid. Smokers can enjoy the feel of smoking, with no fire hazard since there is no need for igniting.

DESCRIPTION OF DRAWINGS

FIG. 1 is the side section view of an electronic cigarette.
FIG. 2 is the section view of the housing (a) separated from the cigarette bottle assembly.
FIG. 3 is the diagram of the axial structure of the cigarette bottle assembly, illustrating the ventilating groove on the peripheral surface of the cigarette holder housing.
FIG. 4 is the side section view of the cigarette bottle assembly, illustrating the structure of the air channel.

SPECIFIC MODE FOR CARRYING OUT THE INVENTION

Figure 5:
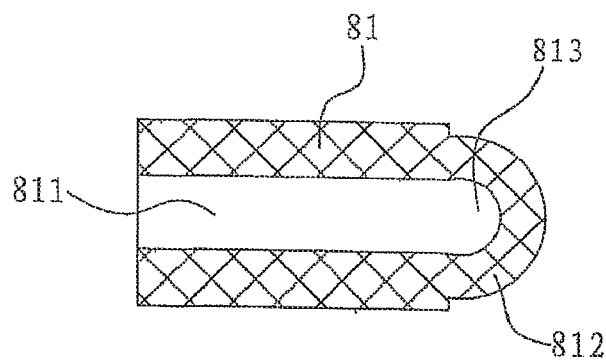
FIG. 5 is the side section view of a porous component of the atomizer.

As shown in FIGS. 1-10, an aerosol electronic cigarette includes a battery assembly, an atomizer assembly and a cigarette bottle assembly, and also includes a shell or housing (a), which is hollow and integrally formed. The battery assembly connects with the atomizer assembly and both are located in the shell. The cigarette bottle assembly is located in one end of the shell, which is detachable. The cigarette bottle assembly fits with the atomizer assembly. The shell has through-air-inlets (a1).

In this specific embodiment, the battery assembly includes the battery, and the operating indicator (1), electronic circuit board (4), and airflow sensor (5), which are connected with the battery. It also includes a check valve (7). The signal output of the airflow sensor (5) is connected with the said electronic circuit board (4). The battery is a rechargeable battery (3), which may be either a rechargeable polymer lithium ion battery or a rechargeable lithium ion battery. The airflow sensor (5) may be alternatively a semiconductor force-sensitive chip capacitance sensor or an inductance sensor.

The rechargeable battery (3) has a flexibly connected charging plug (2). The blades (21) of the charging plug (2) come out of the other end of the shell (a). Between the charging plug (2) and rechargeable battery (3) is a spring (6), which lies against the body of the rechargeable battery (3) on one end, while its free end lies against the charging plug (2), forming a flexible structure, which buffers the charging plug (2) when plugged for charging, thus protecting the rechargeable battery against any damage. Of course, the rechargeable battery (3) in this embodiment has a charging slot on it, which replaces the structure of charging plug (2) to perform the charging function and protect the rechargeable battery (3) against any damage. The operating indicator (1) is a LED. In this embodiment, there are two LEDs. The electronic circuit board (4) includes an electronic switch circuit, which controls the electric circuit according to the input signals, so that the rechargeable battery (3) electrifies the electric heating rod (82) inside the atomizer (8) and the LEDs as well.

As shown in FIGS. 1 and 2, the airflow sensor (5) has a silica gel corrugated membrane (53), which connects with magnetic steel (54) with a reed relay (52) on one of its ends. Both ends of the said reed relay (52) correspond to the relay electrodes (51) respectively.

Figure 6:
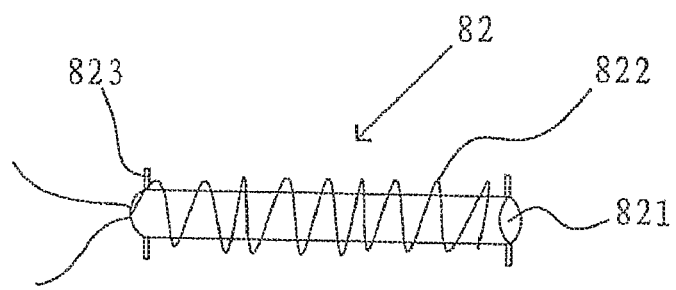
FIG. 6 is the diagram of the structure of an electric heating rod of the atomizer.
Figure 7:
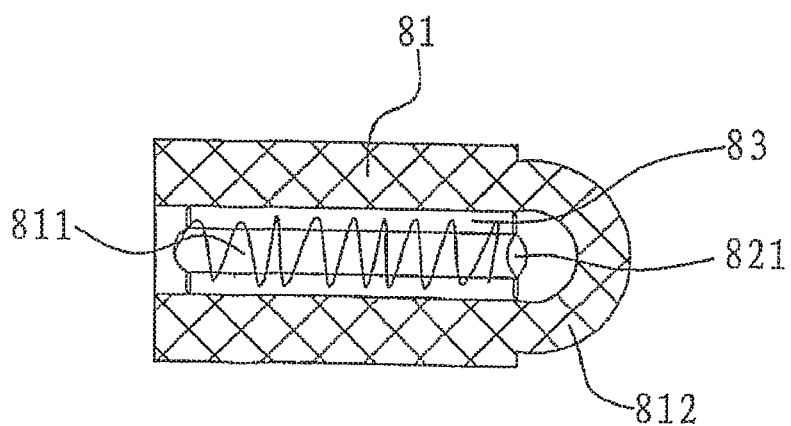
FIG. 7 is the side section of the atomizer, illustrating the locations of and connection relation between the electric heating rod and porous component.
Figure 8:
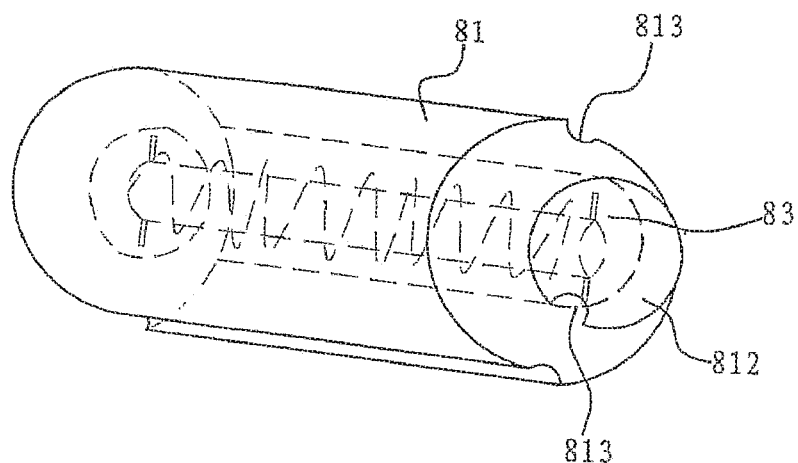
FIG. 8 is the diagram of the atomizer, illustrating the locations of and connection relation between the electric heating rod and porous component.
Figure 9:
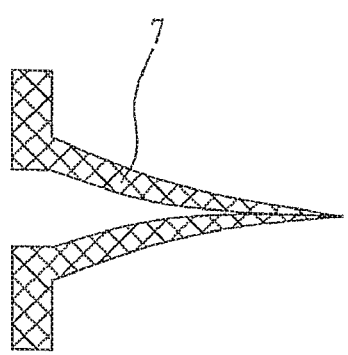
FIG. 9 is the section view of a check valve.
Figure 10:
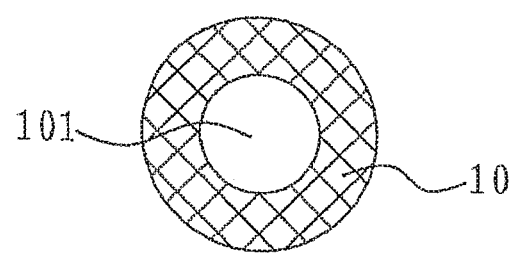
FIG. 10 is the front section view of a restriction component in a second embodiment.
Figure 11:
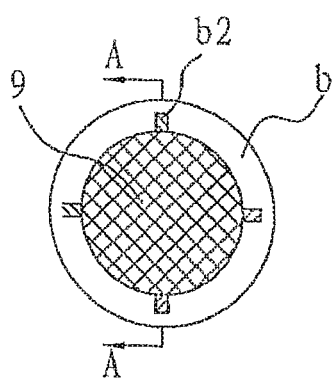
FIG. 11 is a diagram of the axial structure of the cigarette bottle assembly in another embodiment.
Figure 12:
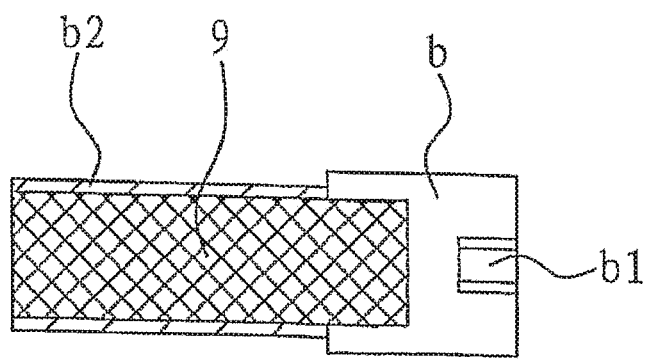
FIG. 12 is a sectional view taken along line A-A of FIG. 11.
Figure 13:
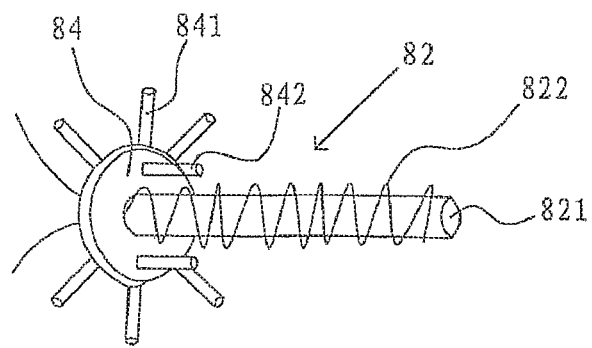
FIG. 13 is a diagram of the structure of the electric heating rod of the atomizer in another embodiment.
Figures 14, 15:
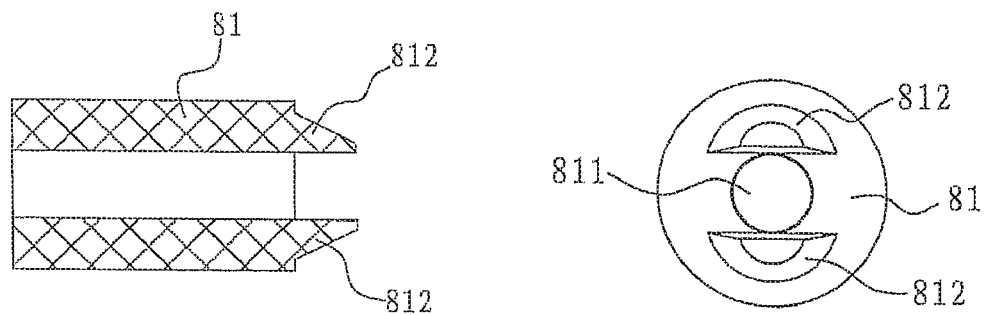
FIG. 14 is a section view of the porous component of the atomizer in the embodiment shown in FIG. 13.
FIG. 15 is a diagram of the axial structure of FIG. 14.
Figure 16:
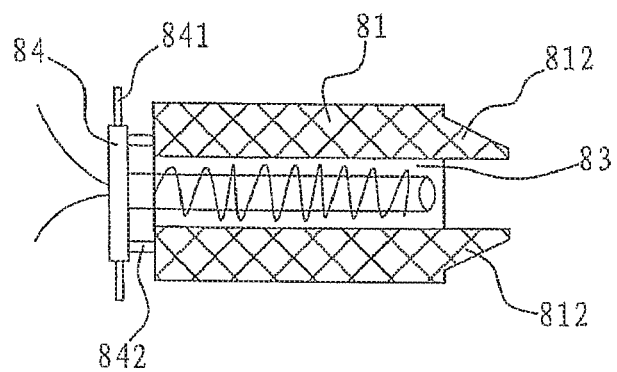
FIG. 16 is a side section view of the atomizer in the embodiment of FIG. 13, illustrating the locations of and connection relation between the electric heating rod and porous component.

As shown in FIGS. 5-8, the atomizer assembly is an atomizer (8), which includes a porous component (81) and a heating rod (82). The body of the porous component (82) has a run-through atomizing chamber (811). The diameter of the electric heating rod (82) is less than the diameter of the atomizing chamber (811). The electric heating rod (82) enters into the atomizing chamber (811), and there is a clearance between the electric heating rod (82) and interior wall of the atomizing chamber (811), which forms a negative pressure cavity (83). One end of the porous component (81) fits with the cigarette bottle assembly. As FIGS. 5, 7 and 8 show, the porous component (81) has a protuberance (812) on the other end, and the protuberance (812) fits with the cigarette bottle assembly. The protuberance (812) is a protruding half sphere, on the side of which there is a run-through hole (813) connecting to the atomizing chamber (811). Of course, the protuberance (812) may also be a taper, rectangle or any other shape. The porous component (81) is made of foamed nickel, stainless steel fiber felt, macromolecular polymer foam or foamed ceramics, providing the remarkable capabilities in liquid absorption and diffusion, and the ability to absorb the liquid stored in the cigarette bottle assembly.

As shown in FIG. 6, the electric heating rod (82) includes a cylinder (821). The heating wire (822) is wound on the wall of the cylinder (821). On the wall of both ends of the cylinder (821), there are mandrils (823) respectively, which lie against the interior wall of the atomizing chamber (811) of the porous component (81). There is a negative pressure cavity (83) between the electric heating rod and interior wall of the atomizing chamber.

The heating wire is made of platinum wire, nickel-chromium alloy wire or iron-chromium alloy wire containing rare earth, or is flaked. The electric heating rod (82) may alternatively have on its peripheral wall the heating layer made of electrically conductive ceramic PTC material, to replace the heating wire.

In this embodiment, the battery assembly and atomizer assembly are mutually connected and then installed inside the integrally formed shell (a) to form a one-piece part. The rechargeable battery (3) may be charged without frequent change of battery. The user just needs to plug the cigarette bottle assembly into the open end of the shell (a), for easy use and very easy change.

As shown in FIGS. 3 and 4, the cigarette bottle assembly includes a hollow cigarette holder shell (b), and a perforated component for liquid storage (9) inside the shell (b). The perforated component for liquid storage (9) is made of such materials as PLA fiber, terylene fiber or nylon fiber, which are suitable for liquid storage. Alternatively, it may be plastic foam molding or column of multi-layer plates made through plastic injection with polyvinyl chloride, polypropylene and polycarbonate. One end of the cigarette holder shell (b) plugs into the shell (a), and the outer peripheral surface of the cigarette holder shell (b) has an inward ventilating groove (b2). On one end surface of the cigarette holder shell (b), there is an air channel (b1) extending inward. The air channel (b1) is located in the center on the surface of one end of shell (b).

As shown in FIGS. 1-9, one end of the porous component (81) lies against one end surface of the perforated component for liquid storage (9), and contacts the perforated component for liquid storage (9). It absorbs the cigarette liquid from the perforated component for liquid storage (9). When the smoker smokes, the cavity of the cigarette holder shell (b) is in the negative pressure state. In the shell (b), one end of the airflow sensor (5) forms a normal pressure cavity, while the other end forms a negative pressure cavity. The air pressure difference between the normal pressure cavity and negative pressure cavity or the high-speed airflow enables the magnetic steel (54) of the airflow sensor (5) to drive the reed relay (52) to contact the relay electrode (51).

Figure 20:
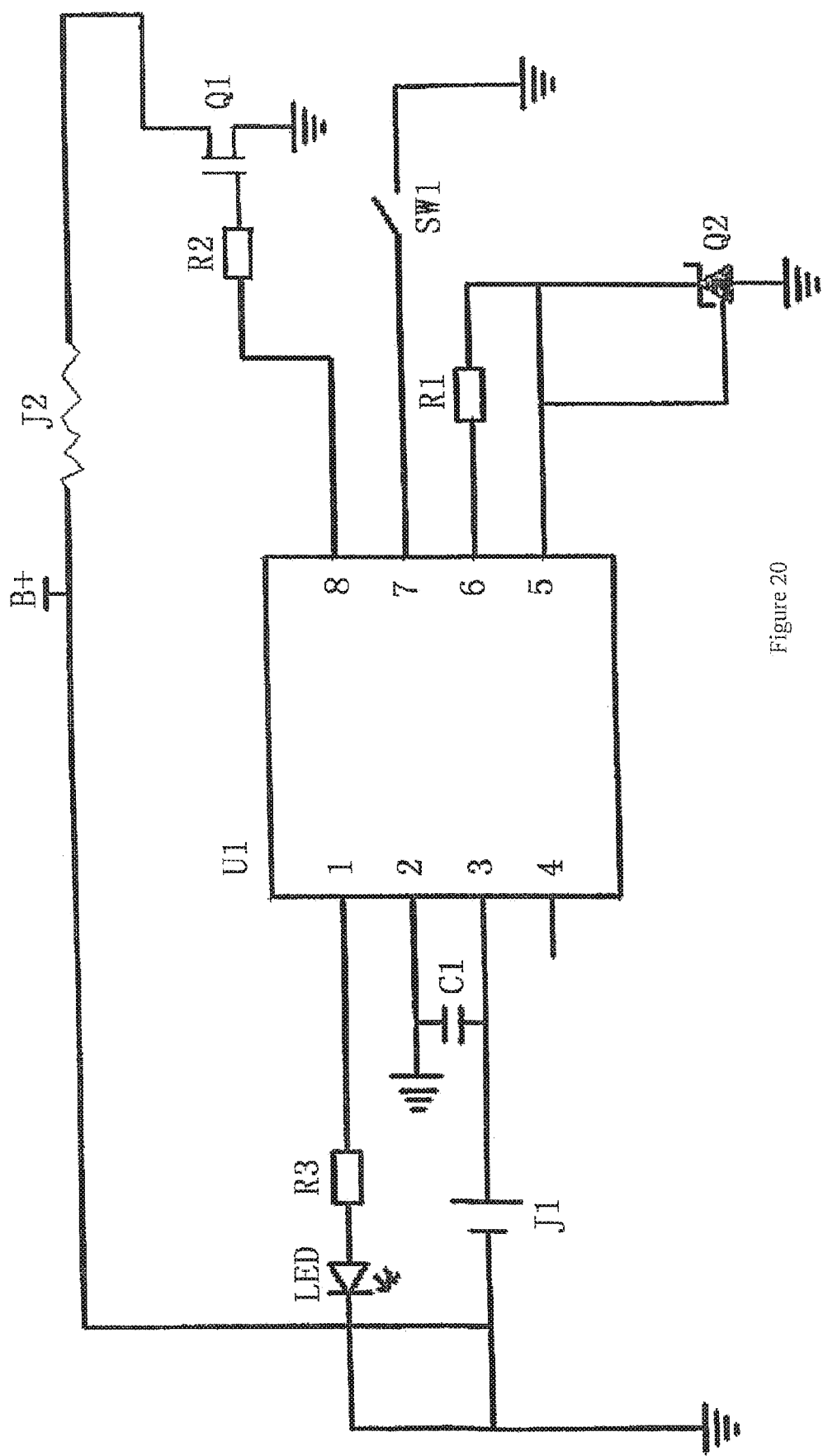
FIG. 20 is the electric circuit diagram of an electronic cigarette.

As shown in FIG. 20, the electric circuit is electrified, and the electronic switch circuit on the electronic circuit board (4) is electrified. Thus, the rechargeable battery (3) starts to electrify the electric heating rod (82) inside the atomizer (8), and at the same time, the LEDs, which are electrified by the rechargeable battery (3), emit light. The air enters the normal pressure cavity through the air inlet (a1), passes the check valve (7) via the airflow passage in the airflow sensor (5), and flows to the negative pressure cavity (83) in the atomizer (8). Since the negative pressure cavity (83) provides the negative pressure compared with the outside, the air flow sprays into it, bringing the cigarette liquid from the porous component (81) to spray into the negative pressure cavity (83) in the form of fine drops.

In the meantime, the electric heating rod (82) is electrified by the rechargeable battery (3) under the control of electronic circuit board (4), to heat the fine drops for atomization. After atomization, the big-diameter fine drops are re-absorbed by the porous component (81) under the action of vortex, while the small-diameter fine drips are suspended in the airflow to form aerosol, which is discharged through the negative pressure cavity (83) and run-through hole (813), flows into the cigarette holder shell (b) of the cigarette bottle assembly, and is absorbed by the air channel (b1). When the aerosol enters the cigarette holder shell (b), multiple small liquid drops are condensed into bigger ones, which fall into the clearance between the cigarette holder shell (b) and air channel (b1) without being absorbed by the air channel (b1). The perforated component for liquid storage (9) of the cigarette bottle assembly and the porous component (81) of the atomizer (8) contact each other to achieve the capillary impregnation for liquid supply.

The unit and its connecting structure of this invention may also be loaded with drugs for delivery to the lung.

Figure 22:
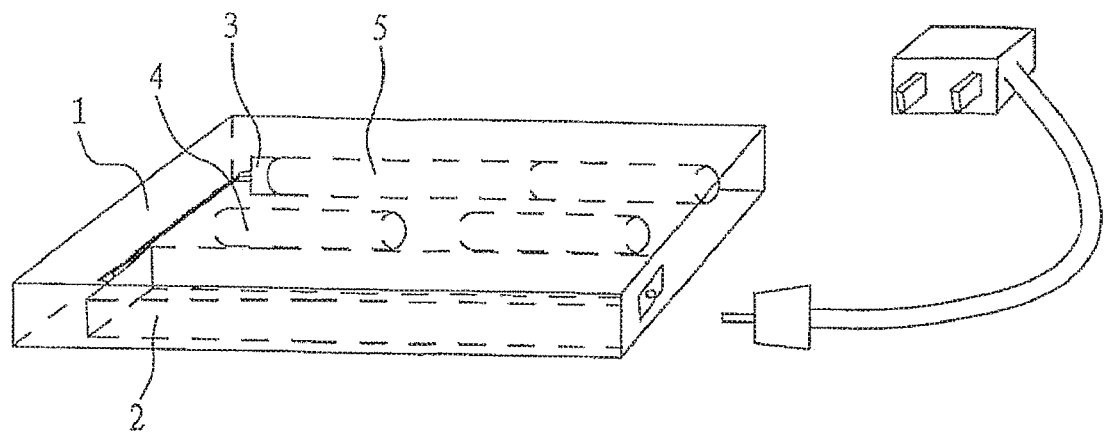
FIG. 22 is a diagram of a charging device, illustrating the locations of and connection relation of various internal parts.
Figure 23:
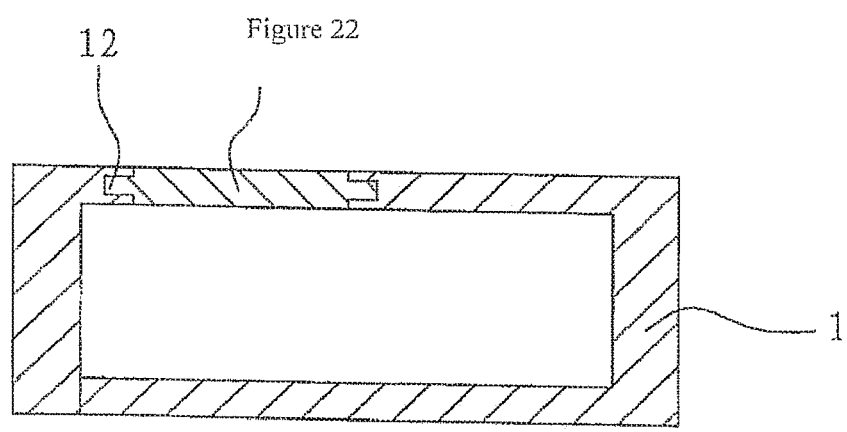
FIG. 23 is the side section view of the charging device.
Figure 24:
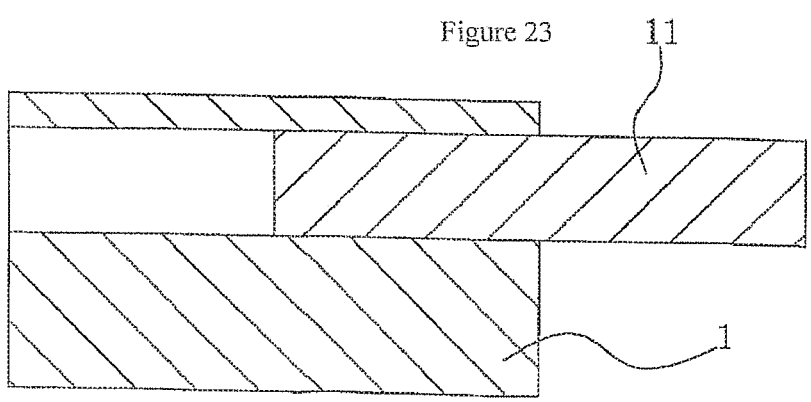
FIG. 24 is the diagram of the front structure of the charging device.

As shown in FIGS. 22, 23 and 24, the electronic cigarette (5) is held in a charging device. The charging device includes a case (1), which contains an auxiliary charging storage battery (2) inside it, and holds the electronic cigarette (5) and the charger (3) for the rechargeable battery embedded in the electronic cigarette (5), as well as the power supply circuit. The power inputs of the auxiliary charging storage battery (2) and charger (3) are connected with the power supply respectively. The charger (3) in this embodiment is a constant voltage & current charger. It may be a GY5210 charger, or any other constant voltage & current charger. The case (1) has a spare liquid supply bottle (4) in it. The power output of the auxiliary charging storage battery (2) is connected with the power input of the charger (3). The power output of the charger (3) is a charging slot (31), which fits with the charging plug of the rechargeable battery inside the electronic cigarette, or a charging plug, which fits with the charging slot of the rechargeable battery.

As shown in FIGS. 23 and 24, on the body of the shell (1), there is a pair of slide ways (12) corresponding to the position of the electronic cigarette, and on the slide ways, there is a slide cover (11).

In the second preferred embodiment, a restriction component (10), which is detachable, is set on one end of the porous component (81). There is a restriction hole (101) on the body of the restriction component (10). The restriction hole (101) corresponds to the atomizing chamber (811). The pore diameter of the restriction hole is less than the inner diameter of the atomizing chamber (811) to the extent that the size of the restriction component (10) installed on the porous component (81) varies, for the purpose of airflow capacity control. On the basis of different applications, the restriction component of different sizes and pore diameters may be used.

In the third preferred embodiment of this utility model, as shown in 11 and 12, on the outer peripheral wall of the cigarette shell (b), there is a protruding rib (b2) that is evenly partitioned. The perforated component for liquid storage (9) enters the cigarette holder shell (b) and lies against the protruding rib (b2). Thus, there appears a clearance between the outer peripheral surface of the perforated component for liquid storage (9) and the interior wall of the shell (b). The clearance is for connection the shell (a) and cigarette holder shell (b). When the user smokes, the air channel (b1) absorbs the air to cause airflow inside the shell (a), thus triggering the airflow sensor (5) and eventually starting the electronic cigarette. Also, the atomizer (8) works to atomize the cigarette liquid and produce gas flow, which enters the cigarette holder shell (b).

In the fourth preferred embodiment, as shown in FIGS. 13, 14, 15 and 16, on one end of the cylinder (821), there is a fixed plate (84), whose outer peripheral wall has partitioned supports (841). The outer ends of the supports (841) lie against the interior wall of the shell (a), thus suspending the cylinder (821), which is connected with the fixed plate (84), in the cavity of the shell (a). On the surface of the fixed plate (84), there is a mandril (842), whose front end lies against one end of the porous component (81), so that the fixed plate (84) is separated from the atomizing chamber (811) of the porous component (81). As a result, the run-through hole on one end of the atomizing chamber (811) won't be blocked, and the mist generated in the atomizing chamber (811) can be dispersed. One end of the porous component (81) has two protuberances (812) at the outlet of the atomizing chamber (811). Between the two protuberances (812) is a clearance. The two protuberances (812) lie against the perforated component for liquid storage (9).

Figure 17:
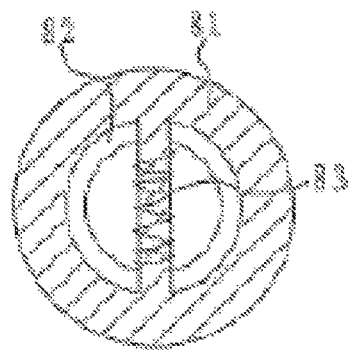
FIG. 17 is a diagram of the axial structure of the atomizer in another embodiment.
Figure 18:
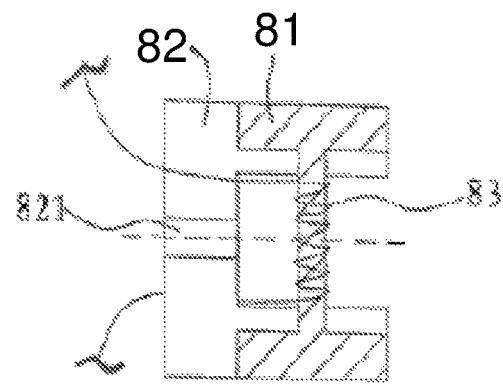
FIG. 18 is the side section view of the atomizer shown in FIG. 17.

In the fifth preferred embodiment, as shown in FIGS. 17 and 18, the atomizer assembly is an atomizer (8), which includes a frame (82), the porous component (81) set on the frame (82), and the heating wire (83) wound on the porous component (81). The frame (82) has a run-through hole (821) on it. The porous component (81) is wound with heating wire (83) in the part that is on the side in the axial direction of the run-through hole (821). One end of the porous component (81) fits with the cigarette bottle assembly. The porous component (81) is made of foamed nickel, stainless steel fiber felt, macromolecular polymer foam or foamed ceramics.

Figure 19:
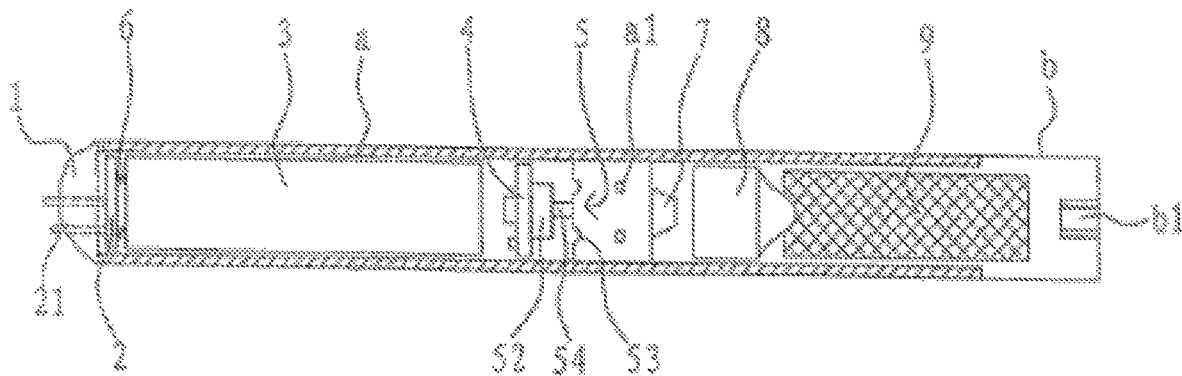
FIG. 19 is the side section view of another electronic cigarette embodiment.
Figure 21:
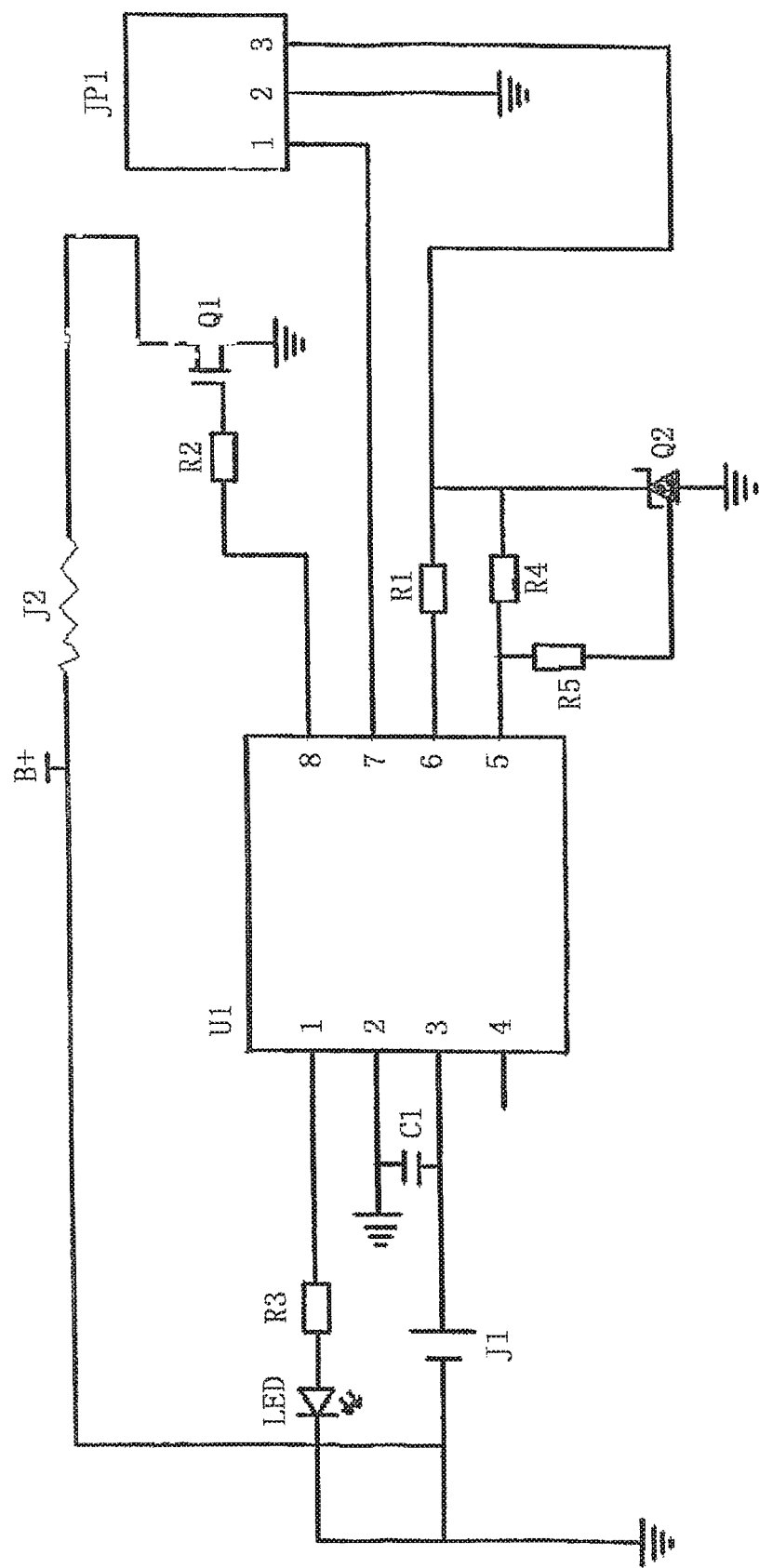
FIG. 21 is another electric circuit diagram of an electronic cigarette.

In the sixth preferred embodiment, as shown in FIG. 19, the airflow sensor (5) has a silica gel corrugated membrane (53), which connects with magnetic steel (54) with a Hall element (52), or a magneto-diode or a magneto-triode on one of its ends. FIG. 21 shows the electric circuit of the electronic cigarette of this solution.

I claim:

1. A vaporizing device comprising:
   a battery assembly including a first housing and a rechargeable battery electrically connected to an electronic circuit board in the first housing;
   a charging connector and an operating indicator in the battery assembly, the charging connector and the operating indicator electrically connected to the electronic circuit board; an atomizer assembly electrically connected to the battery assembly;
   a second housing containing a liquid and having a vapor outlet, the second housing insertable into an open end of the first housing;
   at least one air inlet for allowing air to flow through the atomizer assembly;
   the atomizer assembly including a coil electrically connected to the electronic circuit board, the coil in an atomization chamber, the coil wound around a portion of a porous component, the coil having a central axis perpendicular to a longitudinal axis of the device, with the porous component absorbing liquid contained in the second housing;
   a frame having a first section including a base perpendicular to the longitudinal axis of the device, the base having a through hole to allow air to flow through the frame, the frame having a second section parallel to the longitudinal axis of the device, the second section positioning the porous component on the frame;
   the porous component extending through openings in the second section of the frame, with the portion of the porous component between first and second spaced apart sides of the second section of the frame; and an air flow path from the at least one air inlet, through the atomization chamber to the vapor outlet.

2. The device of claim 1 with a part of the air flow path inside of the second housing.

3. The device of claim 1 further including a restriction component in the air flow path, with the restriction component having an opening with a diameter less than a diameter of the atomization chamber.

4. The device of claim 1 further including an airflow sensor electrically connected to the electronic circuit board.

5. The device of claim 1 wherein the portion of the porous component is parallel to the base of the frame.

6. The device of claim 5 wherein the through hole is aligned with a central section of the coil.

7. The device of claim 6 with a central section of the porous component extending across an opening in the second section of the frame.

8. The device of claim 1 wherein the first housing is an elongate tubular housing.

9. The device of claim 1 including an air channel extending into the second housing from the vapor outlet, and with the vapor outlet located in an end surface of the second housing.

10. A vaporizing device comprising:
a battery assembly including a first housing and a rechargeable battery electrically connected to an electronic circuit board in the first housing;
a charging connector and an operating indicator in the battery assembly, the charging connector and the operating indicator electrically connected to the electronic circuit board;
an atomizer assembly electrically connected to the battery assembly;
a second housing containing a liquid and having a vapor outlet, the second housing insertable into the first housing;
at least one air inlet for allowing air to flow through the atomizer assembly and the second housing;
the atomizer assembly including a wire coil electrically connected to the electronic circuit board, the wire coil in an atomization chamber, the wire coil wound around a portion of a cylindrical porous component, the wire coil having a central axis perpendicular to a longitudinal axis of the device, with the cylindrical porous component absorbing liquid contained in the second housing;
a frame having a first section perpendicular to the longitudinal axis of the device and a second section parallel to the longitudinal axis of the device, with the cylindrical porous component supported on the frame, and the porous component extending through openings in the second section of the frame, with the portion of the cylindrical porous component between first and second spaced apart sides of the frame;
a through hole in the first section of the frame to allow air to flow through the frame;
an air flow path from the at least one air inlet, through the atomization chamber to the vapor outlet; and the vapor outlet at an end of the second housing.

11. The device of claim 10 further including an airflow sensor electrically connected to the electronic circuit board.

12. The device of claim 10 with the through hole aligned with a central section of the cylindrical porous component.

13. A device comprising:
a housing having a first shell and a second shell;
a battery assembly including a rechargeable battery electrically connected to an electronic circuit board in the first shell;
a charging connector at an end of the first shell and an operating indicator in the first shell, the charging connector and the operating indicator electrically connected to the electronic circuit board;
an atomizer assembly electrically connected to the battery assembly;
a vapor outlet and liquid in the second shell, the second shell insertable into an open end of the first shell;
at least one air inlet for allowing air to flow into the housing;
the atomizer assembly including a wire coil electrically connected to the electronic circuit board, the wire coil wound around a section of a porous component perpendicular to a longitudinal axis of the device;
the porous component set on a frame, the porous component extending through openings in the frame, with the section of the porous component between first and second spaced apart sides of the frame;
the porous component absorbing liquid contained in the second shell; and
an air flow path from the at least one air inlet, through a vaporization chamber, to the vapor outlet.

14. The device of claim 13 further including one or more protruding ribs on the outside of the second shell forming part of the air flow path when the second shell is inserted into the first shell.

15. The device of claim 13 further including an inward ventilating groove on the second shell.

16. The device of claim 1 further including an airflow sensor electrically connected to the electronic circuit board.

17. The device of claim 10 wherein the first housing is an elongated tubular housing.

18. A vaporizing device comprising:
a battery assembly including a first housing and a rechargeable battery electrically connected to an electronic circuit board in the first housing;
a charging connector and an operating indicator in the battery assembly, the charging connector and the operating indicator electrically connected to the electronic circuit board;
an atomizer assembly electrically connected to the battery assembly;
a second housing containing a liquid and having a vapor outlet, the second housing insertable into an open end of the first housing;
at least one air inlet for allowing air to flow through the atomizer assembly;
the atomizer assembly including a coil electrically connected to the electronic circuit board, the coil in an atomization chamber, the coil wound around a porous component, the coil having a central axis perpendicular to a longitudinal axis of the device, with the porous component absorbing liquid contained in the second housing;
a frame having a through hole in a flat surface of the frame to allow air to flow through the frame, a portion of the porous component extending through first and second side openings in the frame, and
an air flow path from the at least one air inlet, through the atomization chamber to the vapor outlet.

* * * * *